US008263602B2

(12) United States Patent
Gaines et al.

(10) Patent No.: US 8,263,602 B2
(45) Date of Patent: *Sep. 11, 2012

(54) MATRIX METALLOPROTEINASE INHIBITORS

(75) Inventors: Simon Gaines, Stevenage (GB); Ian Peter Holmes, Stevenage (GB); Stephen Lewis Martin, Stevenage (GB); Stephen Paul Watson, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 528 days.

This patent is subject to a terminal disclaimer.

(21) Appl. No.: 12/266,767

(22) Filed: Nov. 7, 2008

(65) Prior Publication Data

US 2009/0082377 A1    Mar. 26, 2009

Related U.S. Application Data

(63) Continuation of application No. 10/571,443, filed as application No. PCT/EP2004/010319 on Sep. 10, 2004, now Pat. No. 7,601,729.

(30) Foreign Application Priority Data

Sep. 13, 2003  (GB) .................................. 0321538.1

(51) Int. Cl.
*A61K 31/505*  (2006.01)
*A61K 31/405*  (2006.01)
(52) U.S. Cl. ........................................ 514/269; 514/415
(58) Field of Classification Search .................. 514/269, 514/416
See application file for complete search history.

(56) References Cited

U.S. PATENT DOCUMENTS

| 5,789,605 | A | 8/1998 | Smith et al. |
| 6,031,133 | A | 2/2000 | Smith et al. |
| 6,096,904 | A | 8/2000 | Smith et al. |
| 6,242,616 | B1 | 6/2001 | Smith et al. |
| 6,870,058 | B2 | 3/2005 | Smith et al. |
| 7,250,439 | B2 | 7/2007 | Gaines et al. |
| 7,368,585 | B2 | 5/2008 | Smith et al. |
| 7,601,729 | B2 * | 10/2009 | Gaines et al. ................. 514/269 |
| 7,723,536 | B2 | 5/2010 | Smith et al. |
| 2002/0103387 | A1 | 8/2002 | Smith et al. |
| 2005/0065353 | A1 | 3/2005 | Smith et al. |
| 2006/0160875 | A1 | 7/2006 | Gaines et al. |
| 2007/0043223 | A1 | 2/2007 | Smith et al. |
| 2008/0194565 | A1 | 8/2008 | Palle et al. |
| 2009/0187031 | A1 | 7/2009 | Smith et al. |
| 2010/0081610 | A1 | 4/2010 | Sattigeri et al. |

FOREIGN PATENT DOCUMENTS

| EP | 0898566 B1 | 3/1999 |
| WO | WO97/40027 A1 | 10/1997 |
| WO | WO 97/43238 | 11/1997 |
| WO | WO 02/083642 | 10/2002 |
| WO | WO 2004/012663 | 2/2004 |
| WO | WO2004/110974 | 12/2004 |

OTHER PUBLICATIONS

Daheshia (Therapeutic inhibition of matrix metalloproteinases for the treatment of chronic obstructive pulmonary disease (COPD). Current Medical Research and Opinion, 2005, vol. 21, issue 4, pp. 587-593.*
Gueders et al. Matrix metalloproteinases (MMPs) and tissue inhibitor of MMPs in the respiratory tract: Potential implication in asthma and other lung diseases. Eur. J. Pharmacology, 2006, vol. 533, pp. 123-144.*
Hashizume, H. "Synthesis and Biological Activity of New 3-Hydroxy-3-Methylglutaryl-CoA-Synthase Inhibitors", Chem. Pharm. Bull, vol. 42, No. 10, 1994, pp. 2097-2107.
Morales, R. et al. "Crystal Structures of Novel Non-Peptidic, Non-Zinc Chelating Inhibitors Bound to MMP-12", Journal of Molecular Biology, London, GB, vol. 341, No. 4, Aug. 20, 2004, pp. 1063-1076.
Natchus, M.G. et al. "Development of New Carboxylic Acid-Based MMP Inhibitors Derived from Functionalized Propargylglycincs", Journal of Medicinal Chemistry, American Chemical Society, Washington, US, vol. 44, 2001, pp. 1060-1071.
Goodman and Gilman's The Pharmacological Basis of Therapeutics. 10th ed. McGraw Hill Medical Publishing Division 2001, p. 3.
Demedts et al., "Elevated MMP-12 Protein Levels in Induced Sputum from COPD Patients", Thorax, 2006, 61: 196-201.
Russell et al., "Release and Activity of Matrix Metalloproteinase-9 and Tissue Inhibitor of Metalloproteinase-1 by Aveolar Macrophages from Patients with Chronic Obstructive Pulmonary Disease", Am. J. Respir Cell Mol Biol, 2002, 26: 602-9.
Shapiro et al., "Cloning and Characterization of Unique Elastolytic Metalloproteinase Produced by Human Alveolar Macrophages", J. Biol. CHem. 1993, 268: 23824-9.
Brinckerhoff et al., "Matrix Metalloproteinases: A Tail of a Frog That Became a Prince", Nature Rev. Mol. Cell. Biol., 3, 2002, 207-14.
Brinckerhoff, "Joint Destruction in Arthritis: Metalloproteinases in the Spotlight", Arthritis & Rheumatism, 34, 1991, 1073-5.
Belvisi et al., "The Role of Matrix Metalloproteinases (MMPs) in The Pathophysiology of Chronic Obstructive Pulmonary Disease (COPD): A Therapeutic Role for Inhibitors of MMPs?", Inflamm. Res., 52, 2003, 95-190.
Lanone et al., "Overlapping Enzyme-Specific Contributions of Matrix Metalloproteinases-9 and 12 in IL-13-Induced Inflammation and Remodeling", J. Clin. Investigation, 2003, 110, 4, 463-474.
Cox et al., "Matriz Metalloproteinase 9 and The Epidermal Growth Factor Signal Pathway in Operable Non-Small Cell Lung Cancer", Clin. Cancer Res., 2000, 6, 6, 2349-55.
Galligioni et al., "Angiogenesis and Antiangiogenic Agents in Non-Small Cell Lung Cancer", Lung Cancer, 2001, 34 Suppl. 4: 3-7.
Churg A, Wang R, Wang X, Onnervik PO, Thim K, Wright JL. Effect of an MMP-9/MMP-12 inhibitor on smoke-induced emphysema and airway remodelling in guinea pigs. *Thorax* 2007;62(8):706-13.

(Continued)

Primary Examiner — Shengjun Wang
(74) Attorney, Agent, or Firm — Grace C. Hsu; John Lemanowicz

(57) ABSTRACT

The present invention relates to compounds of Formula (I):

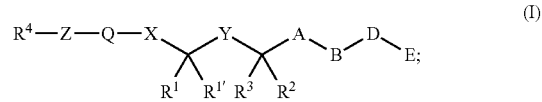

or pharmaceutically acceptable salts thereof, corresponding preparation processes, pharmaceutical formulations and methods for use as inhibitors of matrix metallproteinase enzymes (MMPs).

8 Claims, No Drawings

OTHER PUBLICATIONS

Nenan et al., "Macrophage Elastase (MMP-12): A Pro-Inflammatory Mediator?", Mem. Inst. Oswaldo Cruz, Rio de Janiero, vol. 100 (Suppl. 1): 167-172, 2005, Abstract and p. 168-169).

Shapiro, "Animal Models for COPD.", Chest, 2000 Supplement, 117:223S-227S.

Nenan et al., "Metalloelastase (MMP-12) Induced Inflammatory Response in Mice Airways: Effects of Dexamethasone, Rolipram and Marimastat.", Eur. J. of Pharm., 2007, 559:75-81.

Molet et al., "Increase in macrophage elastase (MMP-12) in lungs from patients with chronic obstructive pulmonary disease.", Inflamm. Res., 2005, 54(1); 31-36.

Hunninghake et al., "MMP12, Lung Function, and COPD In High-Risk Populations,", N. Engl. J. Med., 2009, 361(27):2599-2608.

Hautamaki et al., "Requirement for Macrophage Elastase for Cigarette Smoke-Induced Emphysema in Mice.", Science, 1997, 277:2002-2004.

* cited by examiner

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Fluorescent peptide substrate

<400> SEQUENCE: 1

Gly Pro Leu Gly Leu Phe Ala Arg Lys
 1               5

MATRIX METALLOPROTEINASE INHIBITORS

CROSS REFERENCE TO PRIOR APPLICATIONS

This application is a continuation of U.S. application Ser. No. 10/571,443 filed 13 Mar. 2006 now U.S. Pat. No. 7,601,729 which is a 371 application of PCT/EP2004/010319 filed 10 Sep. 2004 which claims priority to GB0321538.1 filed 13 Sep. 2003.

FIELD OF THE INVENTION

This invention relates to novel chemical compounds, processes for their preparation, pharmaceutical formulations containing them and their use in therapy.

The compounds of the invention are inhibitors of matrix metalloproteinase enzymes (MMPs).

BACKGROUND OF THE INVENTION

Matrix metalloproteinase enzymes play a major role in extracellular matrix component degradation and remodelling. Examples of MMPs include collagenase 1, 2 and 3, gelatinase A and B, stromelysin 1, 2 and 3, matrilysin, macrophage metalloelastase, enamelysin and membrane type 1, 2, 3 and 4 MMP. The enzymes are secreted by connective tissue cells and inflammatory cells. Enzyme activation can not only initiate tissue damage but induce increased inflammatory cell infiltration into the tissue, leading to more enzyme production and subsequent tissue damage. For example, elastin fragments produced by MMP degradation are believed to stimulate inflammation by attracting macrophages to the site of MMP activity. Inhibition of MMPs provides a means for treating disease states wherein inappropriate metalloprotease activity results in degradation of connective tissue and inflammation.

DETAILED DESCRIPTION OF THE INVENTION

In one aspect, the present invention provides compounds of formula (I):

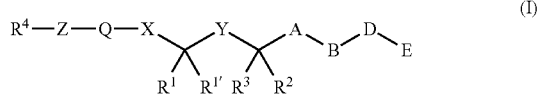

Wherein:
A represents bond, $C_{1-6}$alkyl or CH=CH—$C_{1-4}$alkyl;
B represents bond, O, S, SO, $SO_2$, CO, $CR^7R^8$, $CO_2R^{14}$, $CONR^{14}R^{15}$, $N(COR^{14})(COR^{15})$, $N(SO_2R^{14})(COR^{15})$ or $NR^{14}R^{15}$;
D represents bond, or $C_{1-6}$alkyl;
E represents substituted aryl or substituted or unsubstituted heteroaryl;
Q represents an optionally substituted 5- or 6-membered aryl or heteroaryl ring;
X represents O, S, SO, $SO_2$, CO, $CNR^5$, $CNOR^5$, $CNNR^5R^6$, $NR^{11}$ or $CR^7R^8$;
Y represents $CR^5OR^{11}$, $CR^5SR^{11}$, $NOR^5$, $CR^5NR^6R^{11}$, SO, $SO_2$, CO, $CNR^5$, $CNOR^5$ or CS;
$R^1$ and $R^{1'}$ each independently represents H, $C_{1-6}$alkyl or $C_{1-4}$alkylaryl;

$R^2$ represents $CO_2R^{12}$, $CH_2OR^{12}$ or $CONR^{12}R^{13}$, $CONR^{12}OR^{13}$, $NR^{12}COR^{13}$, SR $PO(OH)_2$, $PONHR^{12}$ or $SONHR^{12}$;
$R^3$ represents H, $C_{1-6}$alkyl or $C_{1-4}$alkylaryl;
$R^4$ represents optionally substituted aryl or heteroaryl;
Z represents a bond, $CH_2$, O, S, SO, $SO_2$, $NR^5$, $OCR^5R^6$, $CR^9R^{10}$ or Z, $R^4$ and Q together form an optionally substituted fused tricyclic group;
$R^5$ and $R^6$ each independently represent H, $C_{1-6}$ alkyl or $C_{1-4}$ alkylaryl;
$R^7$ and $R^8$ each independently represent H, halo, $C_{1-6}$ alkyl or $C_{1-4}$ alkylaryl;
$R^9$ and $R^{10}$ each independently represents H, $C_{1-6}$ alkyl optionally substituted by halo, cyano, $OR^{11}$ or $NR^6R^{11}$, $C_{1-4}$ alkylaryl optionally substituted by halo, cyano, $OR^{11}$ or $NR^6R^{11}$, $OR^{11}$ or, together with the N to which they are attached, $R^9$ and $R^{10}$ form a heterocyclic group optionally containing one or more further heteroatoms selected from O, N and S;
$R^{11}$ represents H, $C_{1-6}$ alkyl, $C_{1-4}$ alkylaryl or $COR^5$;
$R^{12}$ and $R^{13}$ each independently represent H, $C_{1-3}$ alkyl, $C_{1-3}$ alkylaryl or $C_{1-3}$ alkylheteroaryl or, together with the functionality to which they are attached, $R^{12}$ and $R^{13}$ form a heterocyclic group optionally containing one or more further atoms selected from C, O, N and S;
$R^{14}$ and $R^{15}$ each independently represent H, $C_{1-6}$ alkyl, $C_{1-4}$ alkylaryl or $C_{1-4}$ alkylheteroaryl or together with the functionality to which they are attached $R^{14}$ and $R^{15}$ form a heterocyclic or fused heterocyclic group which may contain one or more further atoms selected from C, O, N and S; and physiologically functional derivatives thereof.

References to 'aryl' include references to monocyclic carbocyclic aromatic rings (e.g. phenyl) and bicyclic carbocyclic aromatic rings (e.g. naphthyl) and references to 'heteroaryl' include references to mono- and bicyclic heterocyclic aromatic rings containing 1-3 hetero atoms selected from nitrogen, oxygen and sulphur. In a bicyclic heterocyclic aromatic group there may be one or more hetero-atoms in each of the rings, or only in one ring. Examples of monocyclic heterocyclic aromatic rings include pyridinyl, pyrimidinyl, thiophenyl, furanyl, pyrrolyl, oxazolyl, isoxazolyl, oxadiazolyl, thiazolyl, thiadiazolyl, uracil or imidazolyl, and examples of bicyclic heterocyclic aromatic rings include benzofuranyl, benzimidazolyl, quinolinyl or indolyl. Carbocyclic and heterocyclic aromatic rings may be optionally substituted, e.g. by one or more $C_{1-6}$ alkyl, $C_{2-6}$ alkenyl, halogen, $C_{1-6}$ alkoxy, cyano, hydroxy, nitro, amino, —$N(CH_3)_2$, —$NHCOC_{1-6}$ alkyl, —$OCF_3$, —$CF_3$, —$COOC_{1-6}$ alkyl, —$OCHCF_2$, —$SCF_3$, —$CONR6R7$—$SO_2N(CH_3)_2$, —$SO_2CH_3$ or —$SCH_3$ groups, or by fused cycloalkyl or heterocyclic rings which may themselves be substituted, for example by carbonyl groups.

References to 'alkyl' include references to both straight chain and branched chain aliphatic isomers of the corresponding alkyl. It will be appreciated that references to alkylene and alkoxy shall be interpreted similarly.

Suitably A represents bond or $C_{1-6}$ alkyl, such as $C_2$ or $C_3$ alkyl.

Suitably B represents bond.

Suitably D represents methylene or bond, preferably bond.

For Example A-B-D may suitably represent —$CH_2CH_2$—.

Optional substituents for E include one or more of $C_{1-6}$ alkyl, $C_{2-6}$ alkenyl, halogen, $C_{1-6}$ alkoxy, cyano, hydroxy, nitro, amino, —$N(CH_3)_2$, —$NHCOC_{1-6}$ alkyl, —$OCF_3$, —$CF_3$, —$COOC_{1-6}$ alkyl, —$OCHCF_2$, —$SCF_3$, —$CONR^5R^6$—$SO_2N(CH_3)_2$, —$SO_2CH_3$ or —$SCH_3$ groups, or by fused cycloalkyl or heterocyclic rings which may themselves be substituted, for example by carbonyl groups.

In one subgroup of compounds according to the invention, E represents substituted or unsubstituted 5- or 6-membered heteroaryl such as a nitrogen-containing heteroaromatic group, for example, uracil.

In a further subgroup of compounds according to the invention, E represents aryl, such as phenyl, substituted by a fused substituted or unsubstituted heterocyclic ring, such as a nitrogen-containing heterocyclic ring. Exemplary of this subgroup are compounds according to the invention wherein E represents phthalimido.

Suitable optional substituents for Q include one or more of $C_{1-6}$ alkyl, $C_{2-6}$ alkenyl, halogen, $C_{1-6}$ alkoxy, cyano, hydroxy, nitro, amino, —$N(CH_3)_2$, —$NHCOC_{1-6}$ alkyl, —$OCF_3$, —$CF_3$, —$COOC_{1-6}$ alkyl, —$OCHF_2$, —$SCF_3$, —$CONR^5R^6$—$SO_2N(CH_3)_2$, —$SO_2CH_3$ or —$SCH_3$ groups. Most suitably Q represents unsubstituted phenyl.

Suitably, $R^1$ and $R^{1'}$ each represents hydrogen.
Suitably $R^2$ represents $CO_2R^{12}$, such as $CO_2H$.
Suitably $R^3$ represents hydrogen.
Suitably $R^4$ benzofuranyl, phenyl or pyrimidinyl. Suitable optional substituents for $R^4$ include one or more of $C_{1-6}$ alkyl, $C_{2-6}$ alkenyl, halogen, $C_{1-6}$ alkoxy, cyano, hydroxy, nitro, amino, —$N(CH_3)_2$, —$NHCOC_{1-6}$ alkyl, —$OCF_3$, —$CF_3$, —$COOC_{1-6}$ alkyl, —$OCHF_2$, —$SCF_3$, —$CONR^5R^6$, —$SO_2N(CH_3)_2$, —$SO_2CH_3$ or —$SCH_3$ groups. Preferably $R^4$ represents optionally substituted phenyl or optionally substituted pyrimidinyl.

Suitably X represents $CH_2$.
Suitably Y represents $CHOR^{11}$, where $R^{11}$ suitably represents H, $C_{1-6}$ alkyl or $COR^5$. Preferably $R^{11}$ represents H. $R^5$ preferably represents $C_{1-6}$ alkyl.

Suitably Z represents a bond, or Z, $R^4$ and Q together represent a fused tricyclic group. Preferably, Z represents a bond.

A subgroup of compounds of formula (I) is presented by formula (Ia) and formula (Ib):

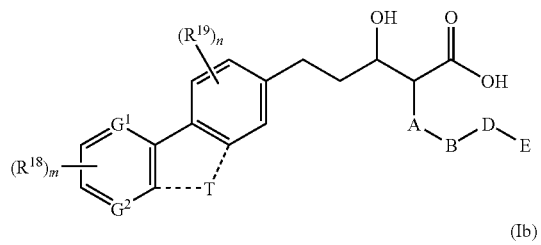

(Ia)

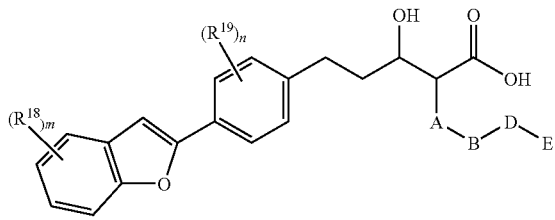

(Ib)

wherein:
T is absent or represents O, S, $NR^{16}$ or $CR^{16}R^{17}$;
--- represents optional bonds;
$G^1$ and $G^2$ each independently represents CH or N;
A represents bond, $C_{1-6}$alkyl or CH=CH—$C_{1-4}$alkyl;

B represents bond, O, S, SO, $SO_2$, CO, $CR^7R^8$, $CO_2R^{14}$, $CONR^{14}R^{15}$, $N(COR^{14})(CoR^{15})$, $N(SO_2R^{14})(COR^{15})$, $NR^{14}R^{15}$;

D represents bond, or $C_{1-6}$ alkyl;

E represents substituted aryl or substituted or unsubstituted heteroaryl;

$R^{16}$ represents H, $C_{1-6}$ alkyl or $C_{1-4}$ alkylaryl;

$R^{17}$ represents H or $C_{1-6}$ alkyl;

$R^{18}$ and $R^{19}$ each independently represents halo, cyano, nitro, $OR^1$, $SR^1$, $COR^{16}$, $NR^{17}COR^{16}$, $CONR^{16}R^{17}$, optionally substituted phenoxy or $C_{1-6}$alkyl optionally substituted by $OR^{16}$;

m and n each independently represents 0 or an integer 1, 2 or 3; and physiologically functional derivatives thereof.

In compounds of formulae (Ia) and (Ib), A suitably represents alkyl, such as $C_{1-4}$alkyl, for example ethyl. Suitably, B represents bond. Suitably D represents bond. Suitably E represents substituted or unsubstituted heteroaryl such as nitrogen-containing heteroaryl, for example uracil, or E represents phenyl substituted by a fused substituted or unsubstituted heterocyclic ring, such as phthalimido.

Preferably n is 0 and m is 1.

Preferably $R^{18}$ represents a para-substituent selected from $NO_2$, $C_{1-6}$ alkyl, $C_{1-6}$ alkoxy, halo, $SC_{1-6}$ alkyl, CN and $COC_{1-6}$ alkyl.

Preferably, $G^1$ and $G^2$ are both CH or both N.

A further subgroup of compounds according to the invention is represented by compounds of formula (Ic):

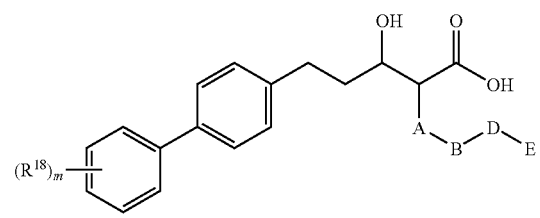

(Ic)

wherein A, B, D, E, $R^{18}$ and m are as defined for formulae (Ia) and (Ib) above; and physiologically functional derivatives thereof.

In compounds of formula (Ic), A-B-D suitably represents —$CH_2$—$CH_2$—. Suitably m represents 0 or 1. When m is 1, $R^{13}$ suitably represents a para substituent selected from $NO_2$, $C_{1-6}$ alkyl, $C_{1-6}$ alkoxy, halo, $SC_{1-6}$ alkyl, CN, $OCF_3$, or $COC_{1-6}$ alkyl.

A further subgroup of compounds according to the intention is represented by compounds of formula (Id):

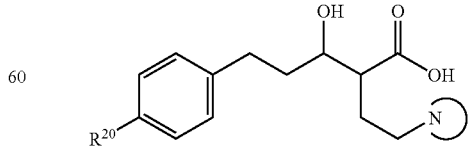

(Id)

wherein $R^{20}$ represents a substituted or unsubstituted aryl or heteroaryl group selected from phenyl, benzofuraryl and pyrimidinyl; and

represents a substituted aryl or a substituted or unsubstituted heteroaryl group comprising at least one nitrogen atom; and physiologically functional derivatives thereof.

In compounds of formula (Id), $R^{20}$ suitably represents unsubstituted or substituted phenyl, unsubstituted benzofuraryl or unsubstituted pyrimidinyl. When $R^{20}$ represents substituted phenyl, suitably the phenyl ring will be substituted by a single substituent in the para position. Suitable substituents include $C_{1-6}$alkyl, $C_{2-6}$alkenyl, halogen, $C_{1-6}$alkoxy, cyano, hydroxy, nitro, amino, —N(CH$_3$)$_2$, —NHCOC$_{1-6}$alkyl, —OCF$_3$, —CF$_3$, —CO$_2$C$_{1-6}$alkyl, OCHCF$_2$, —SCF$_3$, —CONR$^5$R$^6$, —SO$_2$N(CH$_3$)$_2$, —SO$_2$CH$_3$ or —SCH$_3$, such as cyano, COCH$_3$, OCF$_3$ and SCH$_3$.

By the term "physiologically functional derivative" is meant a chemical derivative of a compound of formula (I) having the same physiological function as the free compound of formula (I), for example, by being convertible in the body thereto and includes any pharmaceutically acceptable esters, amides and carbamates, salts and solvates of compounds of formula (I) which, upon administration to the recipient, are capable of providing (directly or indirectly) compounds of formula (I) or active metabolite or residue thereof.

Suitable salts of the compounds of formula (I) include physiologically acceptable salts and salts which may not be physiologically acceptable but may be useful in the preparation of compounds of formula (I) and physiologically acceptable salts thereof. If appropriate, acid addition salts may be derived from inorganic or organic acids, for example hydrochlorides, hydrobromides, sulphates, phosphates, acetates, benzoates, citrates, succinates, lactates, tartrates, fumarates, maleates, 1-hydroxy-2-naphthoates, palmoates, methanesulphonates, formates or trifluoroacetates.

Examples of solvates include hydrates.

When compounds of formula (I) contain chiral centres, the invention extends to mixtures of enantiomers (including racemic mixtures) and diastereoisomers as well as to individual enantiomers. Generally it is preferred to use a compound of formula (I) in the form of a purified single enantiomer. Enantiomerically pure compounds of formula (I) are available by way of chirally selective synthesis or by way of chiral separation.

The compounds of formula (I) and salts and solvates thereof may be prepared by the methodology described hereinafter, constituting a further aspect of this invention.

A first process (A) according to the invention for preparing a compound of formula (I) wherein Z represents a bond comprises reacting a compound of formula (II):

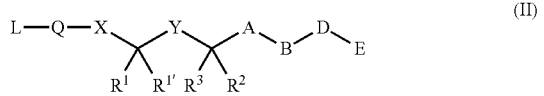

wherein $R^1$, $R^{1'}$, $R^2$, $R^3$, $R^{3'}$, A, B, D, E, Q, X and Y are as previously defined for formula (I) and L represents a leaving group, with a reagent suitable to introduce the group $R^4$, such as a compound $R^4B(OH)_2$, suitably in the presence of a catalyst, such as a noble metal catalyst e.g. palladium, and a suitable base, such as an alkali metal carbonate, e.g. caesium carbonate. The reaction is conveniently carried out in a suitable solvent, such as a polar organic solvent, e.g. dimethyl formamide. Suitable leaving groups represented by L include halides, especially bromide or iodide.

For example, for the synthesis of a (optionally substituted) biphenyl compound according to the invention (i.e. Q and $R^4$ are both phenyl), a phenyl boronic acid may be reacted with [(4-bromophenyl)(methylsulfonyl)amino]acetic acid in the presence of a suitable catalyst:

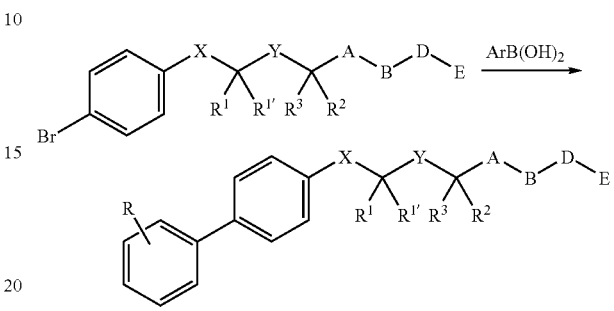

A second process (B) according to the invention for preparing a compound of formula (I) wherein Z represents O, S, SO, SO$_2$, or NR$^5$, comprises reacting a compound of formula (III):

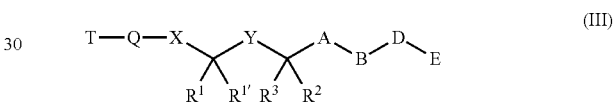

wherein Q, X, Y, $R^1$, $R^{1'}$, $R^2$, $R^3$, A, B, D and E are as previously defined for formula (I), and T represents OH, SH or NR$^6$H, with a reagent suitable to introduce the group $R^4$, such as a compound $R^4$-L, wherein L is a suitable leaving group. The reaction is conveniently carried out in a suitable solvent, such as a solvent containing a heteroatom, e.g. pyridine in the presence of a suitable catalyst, for example a palladium catalyst (preferred for T=NR$^5$H) or a copper catalyst (preferred for T=OH or SH). Suitable leaving groups represented by L include halides, especially bromide or iodide.

For compounds in which Z represents SO or SO$_2$, the compound of formula (I) may conveniently be prepared by initial preparation of the compound in which Z represents S, followed by oxidation of the sulphide to the sulfoxide or the sulfone. The oxidation step may be carried out using methods known in the art such as oxidation with hydrogen peroxide in the case of the sulfone, or oxidation with Oxone® (potassium peroxymonosulfate) in the case of the sulfoxide.

A third process (C) according to the invention for preparing a compound of formula (I) wherein Z represents OCR$^5$R$^6$, comprises reacting a compound of formula (IV):

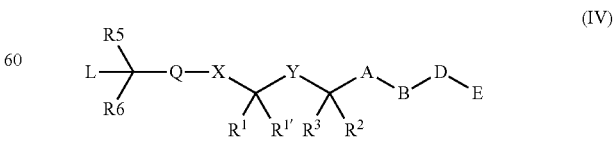

wherein Q, X, Y, $R^1$, $R^{1'}$, $R^2$, $R^3$, $R^5$, $R^6$, A, B, D and E are as previously defined for formula (I), with a reagent suitable to introduce the group $R^4$—O such as a compound $R^4$—OH.

The reaction is conveniently carried out in a suitable solvent, such as an alcohol solvent, e.g. ethanol, under basic conditions, for example in the presence of an aqueous hydroxide such as sodium hydroxide. Suitable leaving groups represented by L include halides, especially bromide or iodide.

A fourth process (D) according to the invention for preparing a compound of formula (I) wherein Z represents $CR^5R^6O$, comprises reacting a compound of formula (V):

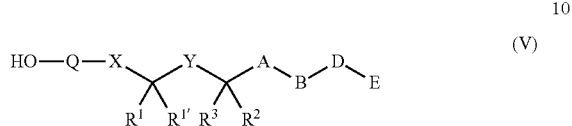

(V)

wherein Q, X, Y, $R^1$, $R^{1'}$, $R^2$, $R^3$, A, B, D and E are as previously defined for formula (I), with a reagent suitable to introduce the group $R^4CR^5R^6$ such as a compound $R^4CR^5R^6$-L, wherein L is a suitable leaving group. The reaction is conveniently carried out in a suitable solvent, such as an alcohol solvent, e.g. ethanol, under basic conditions, for example in the presence of an aqueous hydroxide such as sodium hydroxide. Suitable leaving groups represented by L include halides, especially bromide or iodide.

A fifth process (E) according to the invention for preparing a compound of formula (I) wherein Z represents $CH_2$, comprises reacting a compound of formula (VI):

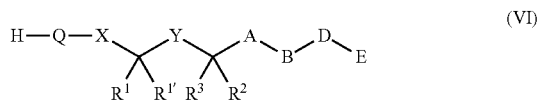

(VI)

wherein Q, X, Y, $R^1$, $R^{1'}$, $R^2$, $R^3$, A, B, D and E are as previously defined for formula (I), with a reagent suitable to introduce the group $R^4CH_2$, such as a compound $R^4CH_2$-L, wherein L is a suitable leaving group, for example halide, suitably in the presence of a catalyst, for example a Lewis acid catalyst such as $AlCl_3$. A Friedel-Crafts reaction may accordingly be appropriate.

A sixth process (F) according to the invention for preparing a compound of formula (I) comprises reacting a compound of formula (VII)

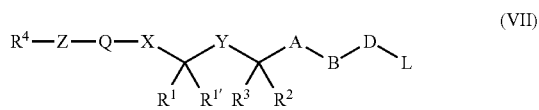

(VII)

wherein Q, X, Y, $R^1$, $R^{1'}$, $R^2$, $R^3$, $R^4$, A, B and D are as previously defined for formula (I), with a reagent suitable to introduce the group E such as a compound H-E. The reaction is conveniently carried out in a suitable solvent, such as an aprotic solvent, e.g. dimethylformamide, under basic conditions, for example in the presence of a base such as potassium hydride. Suitable leaving groups represented by L include halides, such as bromide or iodide, and methylsulphonyloxy groups.

A seventh process (G) according to the invention comprises carrying out a process selected from processes (A) to (F) followed by interconversion of one or more functional groups. Interconversion processes include processes such as oxidation, reduction, substitution, deprotection etc., standard in the art of synthetic chemistry.

Compounds of formula (II), (III), (IV), (V) and (VI) may be prepared by reaction of compounds of formula (VIII):

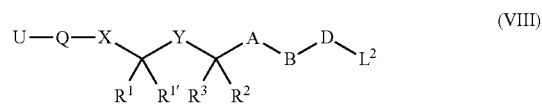

(VIII)

wherein Q, X, Y, $R^1$, $R^{1'}$, $R^2$, $R^3$, A, B and D are as previously defined for formula (I) and U is L in the case of compound (II), T in the case of compound (III), $L(R^5)(R^6)CH_2$ in the case of compound (IV), OH in the case of compound (V) and H in the case of compound (VI), and $L^2$ represents a leaving group more labile than L, with a compound of formula E-H or a salt of formula $E^-M^+$. Suitable leaving groups represented by $L^2$ include halides, such as bromide or iodide, and methylsulphonyloxy groups. Alternatively, an activated leaving group $L^2$ of the Mitsunobu type may be generated by reacting a corresponding alcohol with diisopropylazodicarboxylate and triphenylphosphine; that leaving group may then be displaced by an anion $E^-M^+$ to generate the product.

Compounds of formula (VIII) may in turn be prepared by reaction of compounds of formula (IX):

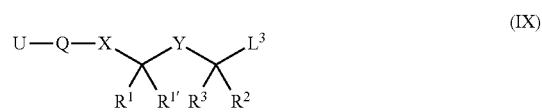

(IX)

wherein Q, X, Y, $R^1$, $R^{1'}$, $R^2$ and $R^3$ are as previously defined for formula (I), U is as previously defined for formula (VIII) and $L^3$ represents a leaving group, with a compound of formula $H-A-B-D-L^2$. The reaction is conveniently carried out in a suitable solvent, such as an aprotic solvent, e.g. dimethylformamide in the presence of a suitable catalyst, for example a metal hydride.

Compounds of formula (IX) may in turn be prepared by reaction of compounds of formula (X) with compounds of formula (XI):

(X)

(XI)

wherein Q, X, Y, $R^1$, $R^{1'}$, $R^2$ and $R^3$ are as previously defined for formula (I), U is as previously defined for formula (VIII), $L^3$ is as previously defined for formula (IX), and $L^4$ represents a leaving group. The reaction is conveniently carried out in a suitable solvent, such as an aprotic solvent, e.g. tetrahydrofuran in the presence of a suitable catalyst, for example a metal hydride.

Analogously, compounds of formula (VII) may be prepared by reaction of compounds of formula (XII):

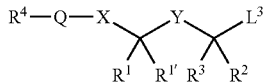

(XII)

wherein Q, X, Y, R$^1$, R$^{1'}$, R$^2$, R$^3$ and R$^4$ are as previously defined for formula (VII), and L$^3$ represents a leaving group, with a compound of formula H-A-B-D-L. The reaction is conveniently carried out in a suitable solvent, such as an aprotic solvent, e.g. dimethylformamide in the presence of a suitable catalyst, for example a metal hydride.

Compounds of formula (XII) may in turn be prepared by reaction of compounds of formula (XIII) with compounds of formula (XIV):

R$^4$—Q—X—L$^4$  (XIII)

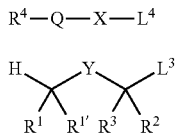

(XIV)

wherein Q, X, Y, R$^1$, R$^{1'}$, R$^2$, R$^3$ and R$^4$ are as previously defined for formula (I) L$^3$ is as previously defined for formula (XII), and L$^4$ represents a leaving group. The reaction is conveniently carried out in a suitable solvent, such as an aprotic solvent, e.g. tetrahydrofuran in the presence of a suitable catalyst, for example a metal hydride.

Compounds of formula R$^4$B(OH)$_2$, R$^4$-L, R$^4$—OH, R$^4$CR$^5$R$^6$-L, R$^4$CH$_2$-L, H-E, H-A-B-D-L$^2$, (X), (XI), (XIII) and (XIV) are known or may be prepared from known compounds by methods familiar to those skilled in the art.

Depending on the identity of the group X, group Y, group R$^2$, L, L$^2$, L$^3$ and L$^4$ it may be preferable for one or more of those groups to be protected during one or more steps of the synthesis of a compound of formula (I). Suitable protecting groups are known to those skilled in the art. Protecting groups may be any conventional protecting groups, for example as described in "Protective Groups in Organic Synthesis" by Theodora Greene and Peter G. M. Wuts (John Wiley and Sons Inc. 1999).

Enantiomeric compounds of the invention may be obtained (a) by the separation of the components of the corresponding racemic mixture, for example, by chiral chromatography, enzymatic resolution methods or preparing and separating suitable diastereoisomers, (b) by direct synthesis from the appropriate chiral starting materials by the methods described above, or (c) by methods analogous to those described above using chiral reagents.

Optional conversion of a compound of formula (I) to a corresponding salt may conveniently be effected by reaction with the appropriate acid or base. Optional conversion of a compound of formula (I) to a corresponding solvate or other physiologically functional derivative may be effected by methods known to those skilled in the art.

Compounds of formula (I) may be useful for the treatment of any conditions in which inhibition of matrix metalloproteinase would be beneficial, especially in the treatment of inflammatory diseases and autoimmune disorders.

Examples of inflammatory conditions and autoimmune disorders in which the compounds of the invention have potentially beneficial effects include diseases of the respiratory tract such as asthma (including allergen-induced asthmatic reactions), cystic fibrosis, bronchitis (including chronic bronchitis), chronic obstructive pulmonary disease (COPD), adult respiratory distress syndrome (ARDS), chronic pulmonary inflammation, rhinitis and upper respiratory tract inflammatory disorders (URID), ventilator induced lung injury, silicosis, pulmonary sarcoidosis, idiopathic pulmonary fibrosis, bronchopulmonary dysplasia, arthritis, e.g. rheumatoid arthritis, osteoarthritis, infectious arthritis, psoriatic arthritis, traumatic arthritis, rubella arthritis, Reiter's syndrome, gouty arthritis and prosthetic joint failure, gout, acute synovitis, spondylitis and non-articular inflammatory conditions, e.g. herniated/ruptured/prolapsed intervertebral disk syndrome, bursitis, tendonitis, tenosynovitic, fibromyalgic syndrome and other inflammatory conditions associated with ligamentous sprain and regional musculoskeletal strain, inflammatory disorders of the gastrointestinal tract, e.g. ulcerative colitis, diverticulitis, Crohn's disease, inflammatory bowel diseases, irritable bowel syndrome and gastritis, multiple sclerosis, systemic lupus erythematosus, scleroderma, autoimmune exocrinopathy, autoimmune encephalomyelitis, diabetes, tumor angiogenesis and metastasis, cancer including carcinoma of the breast, colon, rectum, lung, kidney, ovary, stomach, uterus, pancreas, liver, oral, laryngeal and prostate, melanoma, acute and chronic leukemia, periodontal disease, neurodegenerative disease, Alzheimer's disease, Parkinson's disease, epilepsy, muscle degeneration, inguinal hernia, retinal degeneration, diabetic retinopathy, macular degeneration, ocular inflammation, bone resorption diseases, osteoporosis, osteopetrosis, graft vs. host reaction, allograft rejections, sepsis, endotoxemia, toxic shock syndrome, tuberculosis, usual interstitial and cryptogenic organizing pneumonia, bacterial meningitis, systemic cachexia, cachexia secondary to infection or malignancy, cachexia secondary to acquired immune deficiency syndrome (AIDS), malaria, leprosy, leishmaniasis, Lyme disease, glomerulonephritis, glomerulosclerosis, renal fibrosis, liver fibrosis, pancreatitis, hepatitis, endometriosis, pain, e.g. that associated with inflammation and/or trauma, inflammatory diseases of the skin, e.g. dermatitis, dermatosis, skin ulcers, psoriasis, eczema, systemic vasculitis, vascular dementia, thrombosis, atherosclerosis, restenosis, reperfusion injury, plaque calcification, myocarditis, aneurysm, stroke, pulmonary hypertension, left ventricular remodeling and heart failure.

Diseases of principal interest include COPD and inflammatory diseases of the respiratory tract and joints and vascular diseases.

It will be appreciated by those skilled in the art that reference herein to treatment extends to prophylaxis as well as the treatment of established conditions.

There is thus provided as a further aspect of the invention a compound of formula (I) or a physiologically acceptable derivative thereof for use in medicine.

According to another aspect of the invention, there is provided the use of a compound of formula (I) or a physiologically acceptable derivative thereof for the manufacture of a medicament for the treatment of inflammatory conditions or autoimmune disorders.

In a further or alternative aspect there is provided a method for the treatment of a human or animal subject suffering from or susceptible to an autoimmune disorder or an inflammatory condition which method comprises administering to said human or animal subject an effective amount of a compound of formula (I) or a physiologically functional derivative thereof.

The compounds according to the invention may be formulated for administration in any convenient way, and the invention therefore also includes within its scope pharmaceutical compositions comprising a compound of formula (I) or a physiologically acceptable derivative thereof together, if desirable, with one or more physiologically acceptable diluents or carriers.

There is also provided a process for preparing such a pharmaceutical formulation which comprises mixing the ingredients.

The compounds according to the invention may, for example, be formulated for oral, inhaled, intranasal, topical, buccal, parenteral or rectal administration, preferably for oral administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

Compounds according to the invention for topical administration may be formulated as creams, gels, ointments or lotions or as a transdermal patch. Such compositions may for example be formulated with an aqueous or oily base with the addition of suitable thickening, gelling, emulsifying, stabilising, dispersing, suspending, and/or colouring agents.

Lotions may be formulated with an aqueous or oily base and will in general also contain one or more emulsifying agents, stabilising agents, dispersing agents, suspending agents, thickening agents, or colouring agents. They may also contain a preservative.

For buccal administration the compositions may take the form of tablets or lozenges formulated in conventional manner.

The compounds may also be formulated as suppositories, e.g. containing conventional suppository bases such as cocoa butter or other glycerides.

The compounds according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

The pharmaceutical compositions according to the invention may also be used in combination with other therapeutic agents, for example anti-inflammatory agents (such as corticosteroids (e.g. fluticasone propionate, beclomethasone dipropionate, mometasone furoate, triamcinolone acetonide or budesonide) or NSAIDs (e.g. sodium cromoglycate, nedocromil sodium, PDE-4 inhibitors, leukotriene antagonists, CCR-3 antagonists, iNOS inhibitors, tryptase and elastase inhibitors, beta-2 integrin antagonists and adenosine 2a agonists)) or beta adrenergic agents (such as salmeterol, salbutamol, formoterol, fenoterol or terbutaline and salts thereof) or antiinfective agents (e.g. antibiotics, antivirals).

It will be appreciated that when the compounds of the present invention are administered in combination with other therapeutic agents normally administered by the inhaled or intranasal route, that the resultant pharmaceutical composition may be administered by the inhaled or intranasal route.

Compounds of the invention may conveniently be administered in amounts of, for example, 0.01 to 100 mg/kg body weight, preferably 0.1 to 25 mg/kg body weight, more preferably 0.3 to 5 mg/kg body weight. The compounds may be given more than once daily to be equivalent to the total daily dose. The precise dose will of course depend on the age and condition of the patient and the particular route of administration chosen and will ultimately be at the discretion of the attendant physician.

No toxicological effects are expected when a compound according to the present invention is administered in the above mentioned dose range.

Compounds of the invention may be tested for in vitro activity in accordance with the following assay:

The fluorescent peptide substrate used in the MMP-12 assay is FAM-Gly-Pro-Leu-Gly-Leu-Phe-Ala-Arg-Lys (TAMRA), where FAM represents carboxyfluorescein, and TAMRA represents tetramethylrhodamine. MMP12 catalytic domain (residues 106-268) protein was expressed in $E.\ coli$ in the form of insoluble inclusion bodies & stored in concentrated solution under denaturing conditions (8M guanidine hydrochloride). Enzyme was refolded into active form in situ by direct dilution into assay reactions. The 51 uL reactions are run in NUNC-brand black, square 384-well plates, each well containing 2 uM substrate, 20 nM enzyme, and 0.001-100 uM inhibitor, in 50 mM HEPES, pH 7.5, 150 mM NaCl, 10 mM $CaCl_2$, 1 uM ZnAc, 0.6 mM CHAPS, and 2% DMSO. Positive control wells contain no inhibitor. Negative control wells are effected by either pre-dispensing the EDTA quench (see below) or by omitting enzyme. Reactions are incubated at ambient temperature for 120 min, then quenched by the addition of 15 uL of 100 mM EDTA. Product formation in each well is quantified by measuring flourescense with a Molecular Devices Acquest. The excitation wavelength is set at 485 nM, and the emmision wavelength is 530 nM. $IC_{50}$ values were obtained by first calculating the percent inhibition (% I) at each inhibitor concentration (% I=100*(1-(1-C2)/($C_1$-$C_2$)), where $C^1$ is the mean of the positive controls, and C2 is the mean of the negative controls), then fitting the % I vs. inhibitor concentration [I] data to: % I=A+((B−A)/(1+((C/[I]^D))), where A is the lower asymptote, B is the upper asymptote, C is the $IC_{50}$ value, and D is the slope factor. When tested in this assay, compounds of Examples 1 to 12 had $IC_{50}$s below 100 micromolar.

The invention may be illustrated by reference to the following examples, which should not be construed as a limitation thereto:

General Experimental Details

LC/MS Data were Obtained Under the Following Conditions:

Column: 3.3 cm×4.6 mm ID, 3 um ABZ+PLUS
Flow Rate: 3 ml/min
Injection Volume: 5 μl
Temp: RT
UV Detection Range: 215 to 330 nm Solvents: A: 0.1% Formic Acid+10 mMolar Ammonium Acetate.
B: 95% Acetonitrile+0.05% Formic Acid

| Gradient: | | |
|---|---|---|
| Time | A % | B % |
| 0.00 | 100 | 0 |
| 0.70 | 100 | 0 |
| 4.20 | 0 | 100 |
| 5.30 | 0 | 100 |
| 5.50 | 100 | 0 |

$^1$HNMR spectra were obtained at 400 MHz on a Bruker-Spectrospin Ultrashield 400 spectrophotometer.

EXAMPLES

Example 1

5-Biphenyl-4-yl-2-[2-(1,3-dioxo-1,3-dihydro-2H-isoindol-2-yl)ethyl]-3-hydroxypentanoic acid

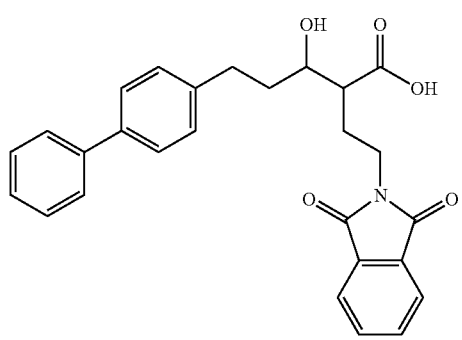

Potassium phthalimide (8.8 mg, 60 μmol) was added in one portion to a stirred solution of 1,1-dimethylethyl 5-(4-biphenylyl)-3-({[4-(methyloxy)phenyl]methyl}oxy)-2-{2-[(methylsulfonyl) oxy]ethyl}pentanoate (28.4 mg, 50 μmol) in dimethylformamide (0.5 mL) under nitrogen at room temperature. The resulting solution was heated at 80° C. for 1 h 45 min then cooled to room temperature. The volatiles were evaporated and the residue taken up in dichloromethane (0.5 mL). Trifloroacetic acid (0.5 mL) was added in one portion and the resulting solution stirred for 1 h at room temperature. The volatiles were evaporated and the residue purified by mass directed auto-preparative HPLC to give the title compound as a white solid (6.0 mg, 27%). LC/MS: 3.43 min; z/e 444, calcd (M+1) 444. $^1$H NMR (400 MHz: $CDCl_3$): 7.85 (2H), 7.70 (2H), 7.55 (1H), 7.50 (1H), 7.45 (2H), 7.30 (1H), 7.25 (4H), 3.85 (3H), 2.95 (1H), 2.75 (1H), 2.60 (1H), 2.20 (1H), 2.05 (1H), 1.90 (2H).

Example 2

5-Biphenyl-4-yl-3-hydroxy-2-[2-(3-methyl-2,6-dioxo-3,6-dihydropyrimidin-1(2H)-yl)ethyl]pentanoic acid

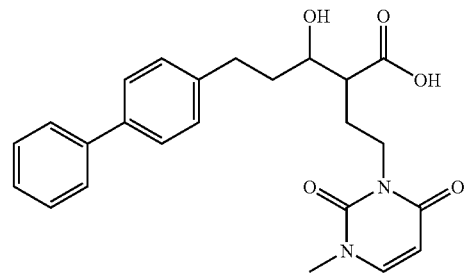

Prepared by an analogous reaction sequence to example 1. LC/MS: 2.96 min; Z/e 423, calcd (M+1) 423.

Example 3

5-Biphenyl-4-yl-3-hydroxy-2-[2-(3-methyl-2,4-dioxo-3,4-dihydropyri midin-1(2H)-yl)ethyl]pentanoic acid

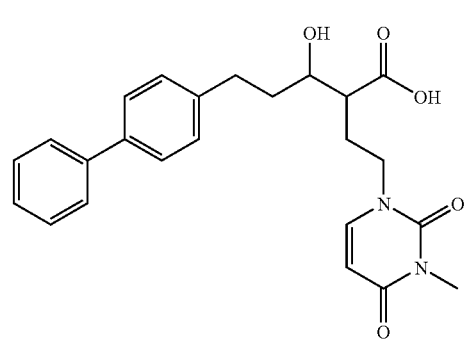

Prepared by an analogous reaction sequence to example 1. LC/MS: 2.98 min; z/e 423, calcd (M+1) 423.

Example 4

5-(4'-Acetyl biphenyl-4-yl)-3-hydroxy-2-[2-(3-methyl-2,4-dioxo-3,4-dihydropyrimidin-1(2H)-yl)ethyl]pentanoic acid

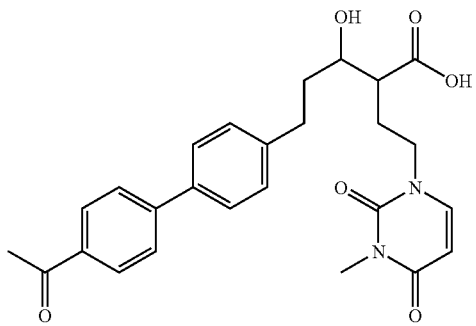

A solution of 3-hydroxy-5-(4-iodophenyl)-2-[2-(3-methyl-2,4-dioxo-3,4-dihydro-1(2H)-pyrimidinyl)ethyl]pentanoic acid (10 mg, 21 µmol) in dimethylformamide (0.5 mL) was added in one portion to a mixture of p-acetylbenzeneboronic acid (4.0 mg, 25 µmol) and fibrecat FC1001 (2.71% Pd; 8.3 mg, 2.0 µmol) in a Smith microwave reaction vial. Aqueous sodium carbonate solution (1.0 M; 53 µL, 53 µmol) was added and the vial capped. The crude reaction mixture was heated at 150° C. for 15 min using a Smith Synthesiser microwave reactor. On cooling the vial was opened and the contents filtered through a Whatman 5 µM filter tube, washing the filter cake with methanol (2×1 mL). The filtrate was evaporated and the resulting residue was purified using mass directed autopreparative reverse phase HPLC to give the title compound (6.0 mg, 61%) as a white solid. LC/MS: 2.82 min; z/e 465, calcd (M+1) 465. H NMR (400 MHz: DMSO-$d_6$): 8.00 (2H), 7.80 (2H), 7.60 (4H), 7.30 (2H), 6.65 (1H), 3.70 (3H), 3.10 (3H), 2.80 (1H), 2.60 (2H), 2.30 (1H), 1.85 (2H), 1.60 (1H).

Example 5

3-Hydroxy-2-[2-(3-methyl-2,4-dioxo-3,4-dihydropyrimidin-1(2H)-yl)ethyl]-5-(4-pyrimidin-5-ylphenyl)pentanoic acid

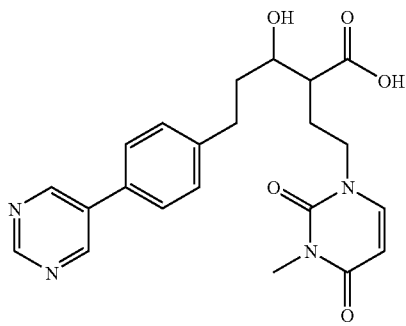

Prepared by an analogous reaction sequence to example 4. LC/MS: 2.27 min; Z/e 425, calcd (M+1) 425.

Example 6

3-Hydroxy-2-[2-(3-methyl-2,4-dioxo-3,4-dihydropyrimidin-1(2H)-yl)ethyl]-5-[4'-(trifluoromethoxy)biphenyl-4-yl]pentanoic acid

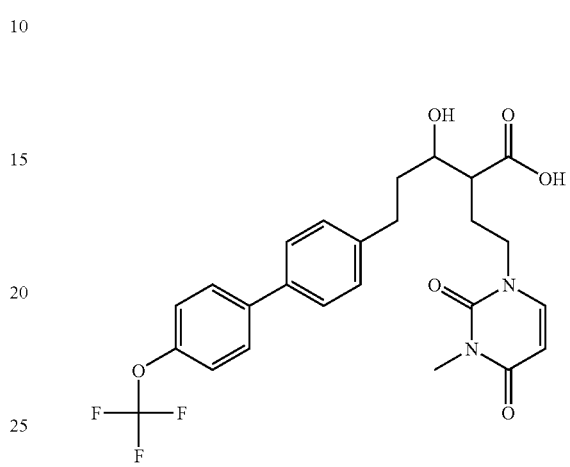

Prepared by an analogous reaction sequence to example 4. LC/MS: 3.28 min; Z/e 506, calcd (M+1) 506.

Example 7

5-[4-(1-Benzofuran-2-yl)phenyl]-2-[2-(1,3-dioxo-1,3-dihydro-2H-isoindol-2-yl)ethyl]-3-hydroxypentanoic acid

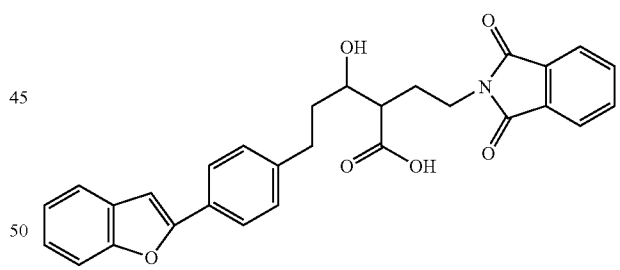

A solution of 2-[2-(1,3-dioxo-1,3-dihydro-2H-isoindol-2-yl)ethyl]-3-hydroxy-5-(4-iodophenyl) pentanoic acid (25 mg, 50 µmol) in dimethylformamide (1.0 mL) was added in one portion to a mixture of -benzofuran-2-ylboronic acid (11 mg, 70 µmol) and fibrecat FC1001 (2.71% Pd; 20 mg, 5.0 µmol) in a Smith microwave reaction vial. Cesium carbonate (41.0 mg, 125 µmol) was added and the vial capped. The crude reaction mixture was heated at 150° C. for 15 min using a Smith Synthesiser microwave reactor. On cooling the vial was opened and the contents partitioned between methanol/dichloromethane (10:90; 10 mL) and aqueous hydrochloric acid solution (2.0 M; 10 mL). The organic phase was separated and filtered through a Whatman 5 μM filter tube, washing the filter cake with methanol (2×1 mL). The filtrate was evaporated and the resulting residue was purified using mass directed auto-preparative reverse phase HPLC to give the title compound (3.0 mg, 12%) as a pale yellow solid. LC/MS: 3.69 min; z/e 484, calcd (M+1) 484. $^1$H NMR (400 MHz: DMSO-$d_6$): 7.80 (6H), 7.65 (2H), 7.30 (5H), 3.65 (1H), 3.60 (2H), 2.75 (1H), 2.55 (1H), 2.40 (1H major), 2.25 (1H minor), 1.85 (2H), 1.65 (2H).

Example 8

2-[2-(1,3-Doxo-1,3-dihydro-2H-isoindol-2-yl)ethyl]-3-hydroxy-5-[4'-(trifluoromethoxy)biphenyl-4-yl]pentanoic acid

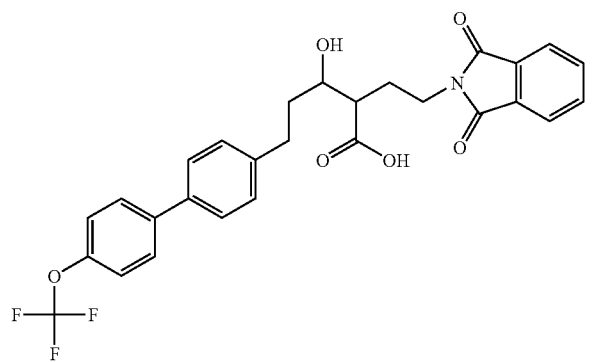

Prepared by an analogous reaction sequence to example 7. LC/MS: 3.72 min; Z/e 528, calcd (M+1) 528.

Example 9

2-[2-(1,3-Dioxo-1,3-dihydro-2H-isoindol-2-yl)ethyl]-3-hydroxy-5-[4'-(methylthio)biphenyl-4-yl]pentanoic acid

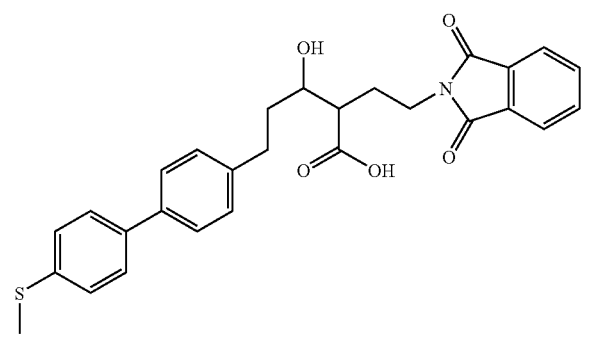

Prepared by an analogous reaction sequence to example 7. LC/MS: 3.61 min; z/e 490, calcd (M+1) 490.

Example 10

5-(4'-Cyanobiphenyl-4-yl)-2-[2-(1,3-dioxo-1,3-dihydro-2H-isoindol-2-yl)ethyl]-3-hydroxypentanoic acid

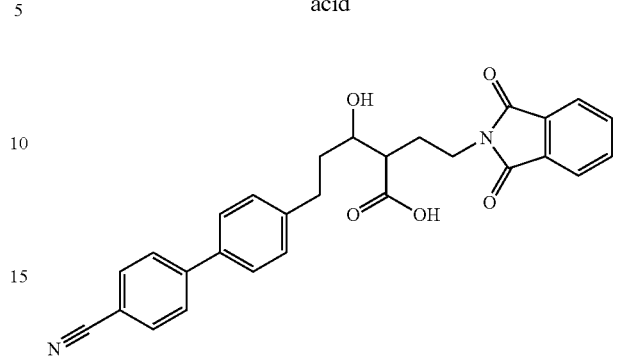

Prepared by an analogous reaction sequence to example 7. LC/MS: 3.34 min; Z/e 469, calcd (M+1) 469.

Example 11

5-(4'-Acetylbiphenyl-4-yl)-2-[2-(1,3-dioxo-1,3-dihydro-2H-isoindol-2-yl)ethyl]-3-hydroxypentanoic acid

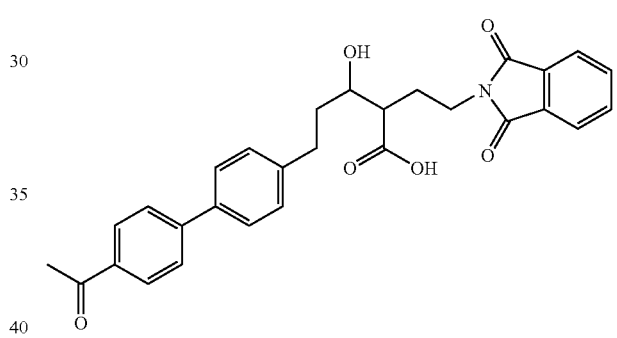

Prepared by an analogous reaction sequence to example 7. LC/MS: 3.28 min; z/e 486, calcd (M+1) 486.

Example 12

2-[2-(1,3-Dioxo-1,3-dihydro-2H-isoindol-2-yl)ethyl]-3-hydroxy-5-(4-pyrimidin-5-ylphenyl)pentanoic acid

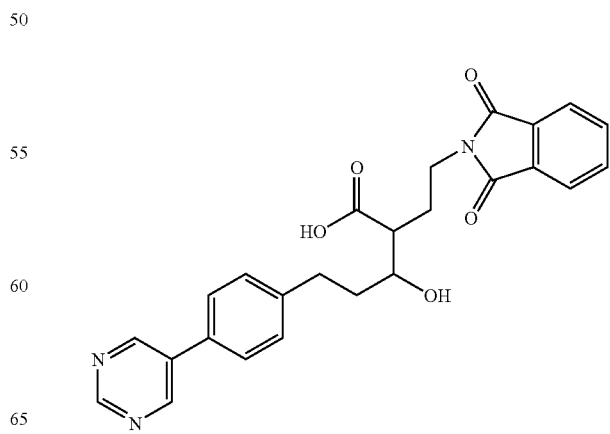

Prepared by an analogous reaction sequence to example 7. LC/MS: 2.70 min; Z/e 446, calcd (M+1) 446.

Intermediate 1: 4-Bromomethyl-biphenyl

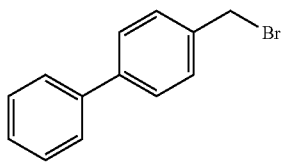

Carbon tetrabromide (8.99 g, 27.1 mmol) and triphenyl phosphine (7.11 g, 27.1 mmol) were added to a stirred solution of biphenyl-4-yl methanol (5.00 g, 27.1 mmol) in dichloromethane (100 mL) at room temperature. Stirring was continued at room temperature for 1.5 hours then the solvent removed by evaporation under reduced pressure. The residue was purified by column chromatography on silica gel (1:20 diethyl ether:cyclohexane) to give the title compound (6.37 g, 95%) as a white solid. $^1$H NMR (400 MHz: CDCl$_3$): 7.6 (4H), 7.45 (4H), 7.35 (1H), 4.55 (2H).

Intermediate 2: 5-Biphenyl-4-yl-3-oxo-pentanoic acid tert-butyl ester

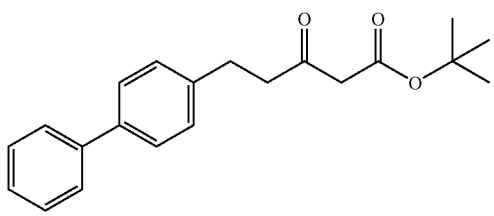

A solution of t-butyl acetoaceate (1.84 mL, 11.1 mmol) in tetrahydrofuran (20 mL) was added to a stirred suspension of sodium hydride (488 mg, 12.2 mmol) in tetrahydrofuran (10 mL) at 0° C. under nitrogen. After stirring for 10 minutes n-butyl lithium (1.6 M in hexanes; 7.3 mL, 11.6 mmol) was added dropwise over 2 minutes then stirring was continued for a further 10 minutes. A solution of 4-bromomethyl-biphenyl (Intermediate 1, 3.00 g, 12.2 mmol) in tetrahydrofuran (6 mL) was added dropwise over 10 minutes and the resulting solution stirred at 0° C. for 1.5 hours. 6 M Hydrochloric acid (15 mL) was added; then the crude reaction mixture was extracted with diethyl ether (3×50 mL). The organic phases were combined, washed with brine (50 mL), dried (MgSO$_4$) then the solvent evaporated under reduced pressure. The residue was purified by column chromatography on silica gel (1:20 diethyl ether:cyclohexane) to give the title compound (1.37 g, 38%) as a yellow solid. LC/MS: 3.78 min; z/e 342, calcd (M+NH$_4$) 342. $^1$H NMR (400 MHz: CDCl$_3$): 7.55 (2H), 7.50 (2H), 7.43 (2H), 7.32 (1H), 7.25 (2H), 3.34 (2H), 2.95 (4H), 1.45 (9H).

Intermediate 3: tert-Butyl 5-biphenyl-4-yl-2-(2-{[tert-butyl(dimethyl)silyl]oxy}ethyl)-3-oxopentanoate

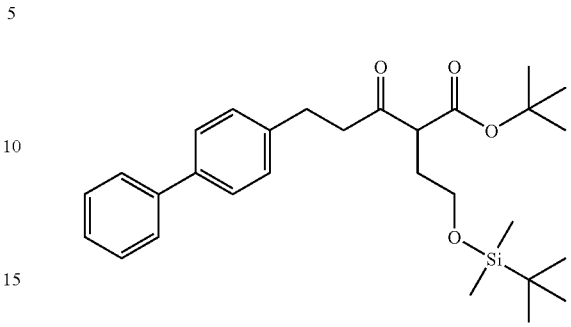

A solution of 5-biphenyl-4-yl-3-oxo-pentanoic acid tert-butyl ester (13.7 g, 42.4 mmol) in dimethylformamide (10 mL) was added dropwise over 20 min to a stirred suspension of sodium hydride (60% mineral oil suspension; 1.78 g, 44.4 mmol) in dimethylformamide (10 mL) at 0° C. under nitrogen. After stirring for 20 min (2-bromoethoxy)-t-butyldimethylsilane (10.0 g, 46.4 mmol) was added dropwise over 20 min at 0° C. then the reaction heated to 70° C. for 2.5 h. On cooling to room temperature the reaction was quenched by careful addition of water (5 mL) then the volatiles evaporated. The residue was partitioned between saturated aqueous ammonium chloride solution (200 mL) and dichloromethane (200 mL) and the phases separated. The aqueous phase was washed with dichloromethane (3×200 mL) then the organic phases combined, washed with brine (200 mL), dried (sodium sulfate) and the solvent evaporated. The residue was chromatographed on silica gel (10% diethyl ether:cyclohexane) to give the title compound (12.1 g, 59%) as colourless oil which was a mixture of diastereomers. LC/MS: 4.70 min; z/e 483, calcd (M+1) 483. $^1$H NMR (400 MHz: CDCl$_3$): 7.55 (2H), 7.50 (2H), 7.40 (2H), 7.35 (1H), 7.25 (2H), 3.60 (2H), 2.95 (3H), 2.20 (1H minor) 2.0 (1H major), 1.55 (1H), 1.45 (11H), 0.85 (9H), 0.5 (6H).

Intermediate 4: tert-Butyl 5-biphenyl-4-yl-2-(2-{[tert-butyl(dimethyl)silyl]oxy}ethyl)-3-hydroxypentanoate

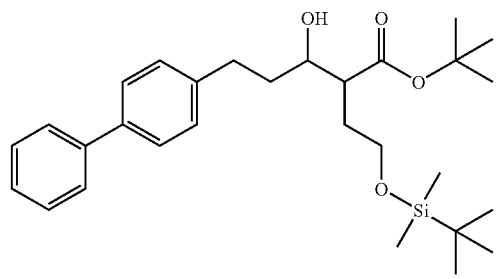

Sodium borohydride (1.05 g, 27.7 mmol) was added portion wise to a stirred solution of tert-butyl 5-biphenyl-4-yl-2-(2-{[tert-butyl(dimethyl)silyl]oxy}ethyl)-3-oxopentanoate (12.1 g, 25.2 mmol) in methanol (80 mL) at 0° C. under nitrogen. On completion of addition stirring was continued for 1.5 h then the reaction was quenched with saturated aqueous ammonium chloride solution (80 mL). The resulting mixture was extracted with diethyl ether (3×200 mL) then the organic layers were combined, washed with brine (100 mL), dried (magnesium sulfate) and the solvent evaporated. The residue was chromatographed on silica gel (10% to 50% diethyl ether:cyclohexane) to give the title compound (8.47 g, 69%) as a colourless oil which was a mixture of diastereomers. LC/MS: 4.49 min; z/e 485, calcd (M+1) 485. $^1$H NMR (400 MHz: CDCl$_3$): 7.60 (2H), 7.50 (2H), 7.45 (2H), 3.90 (1H minor), 3.80 (1H minor), 3.70 (1H major), 3.65 (1H major), 3.25 (1H minor), 3.00 (1H major), 2.90 (1H), 2.75 (1H), 2.60 (1H major), 2.55 (1H minor), 1.90 (1H), 1.85 (2H), 1.45 (10H), 0.90 (9H), 0.5 (6H).

Intermediate 5: 4-Methoxybenzyl 2,2,2-trichloroethanimidoate

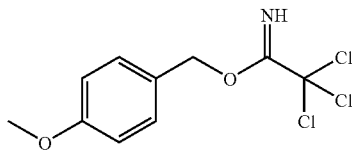

4-Methoxybenzyl 2,2,2-trichloroethanimidoate was prepared using the procedure of Smith, Amos B. Iii; Qiu, Yuping; Kaufman, Michael; Arimoto, Hirokazu; Jones, David R.; Kobayashi, Kaoru; Beauchamp, Thomas J. "Preparation of intermediates for the synthesis of discodermolides and their polyhydroxy dienyl lactone derivatives for pharmaceutical use"—WO 0004865.

Intermediate 6: 1,1-Dimethylethyl 5-(4-biphenylyl)-2-(2-{[(1,1-dimethylethyl) (dimethyl)silyl]oxy}ethyl)-3-({[4-(methyloxy)phenyl]methyl}oxy)pentanoate

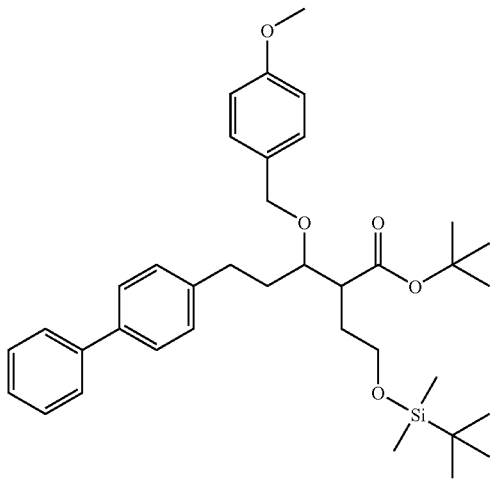

Boron trifluoride etherate (8.0 μL, 65 μmol) was added to a stirred solution of tert-butyl 5-biphenyl-4-yl-2-(2-{[tert-butyl(dimethyl)silyl]oxy}ethyl)-3-hydroxypentanoate (7.88 g, 16.3 mmol) and 4-methoxybenzyl 2,2,2-trichloroethanimidoate (6.88 g, 24.5 mmol) in tetrahydrofuran (40 mL) at 0° C. under nitrogen. The reaction was allowed to warm to room temperature at which stirring was continued for 2 h. A further portion of boron trifluoride etherate (8.0 μL, 65 μmol) was then added and stirring was continued at room temperature for a further 2 h. Two further additions of boron trifluoride etherate (8.0 μL, 65 μmol) followed by stirring at room temperature for 2 h were carried out before evaporation of the solvent. The residue was chromatographed on silica gel (5% to 10% diethyl ether:cyclohexane) to give the title compound (3.39 g, 34%) as a pale yellow oil which was a mixture of diastereomers. LC/MS: 4.81 min; z/e 605, calcd (M+1) 605. $^1$H NMR (400 MHz: CDCl$_3$): 7.55 (2H), 7.45 (4H), 7.35-6.80 (7H), 4.50 (2H), 3.80 (3H), 3.60 (3H), 2.95 (1H), 2.80 (1H), 2.65 (1H), 1.85 (4H), 1.45 (9H), 0.85 (9H), 0.5 (6H).

Intermediate 7: 1,1-Dimethylethyl 5-(4-biphenylyl)-2-(2-hydroxyethyl)-3-({[4-(methyloxy)phenyl]methyl}oxy)pentanoate

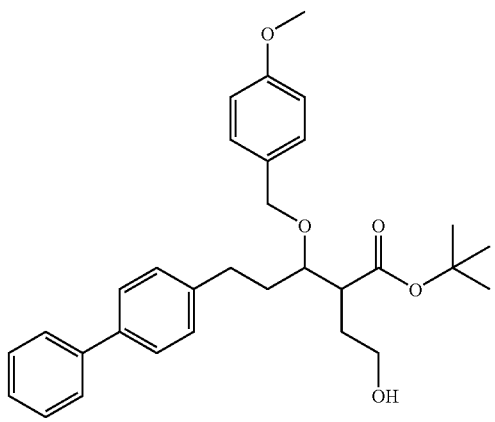

A solution of tetra-n-butylammonium fluoride (1.0 M in THF; 6.2 mL, 6.2 mmol) was added dropwise over 15 min to a stirred solution of 1,1-dimethylethyl 5-(4-biphenylyl)-2-(2-{[(1,1-dimethylethyl) (dimethyl)silyl]oxy}ethyl)-3-({[4-(methyloxy)phenyl]methyl}oxy)pentanoate (3.39 g, 5.61 mmol) in tetrahydrofuran (20 mL) at 0° C. under nitrogen. The reaction was allowed to warm to room temperature at which stirring was continued for 2 h. The volatiles were evaporated and the residue partitioned between ethyl acetate (100 mL) and water (100 mL). The phases were separated and the aqueous layer was washed with ethyl acetate (3×100 mL). The organic layers were combined, washed with brine (100 mL), dried (magnesium sulfate) and the solvent evaporated. The residue was chromatographed on silica gel (50% to 75% diethyl ether:cyclohexane) to give the title compound (1.6 g, 58%) as a yellow oil which was a mixture of diastereomers. LC/MS: 3.98 min; z/e 491, calcd (M+1) 491. $^1$H NMR (400 MHz: CDCl$_3$): 7.55 (2H), 7.45 (4H), 7.30 (5H), 6.90 (2H), 4.50 (2H), 3.80 (3H), 3.65 (2H), 2.80 (2H), 2.65 (1H major), 2.05 (1H minor), 1.85 (3H), 1.60-1.35 (11H).

Intermediate 8: 1,1-Dimethylethyl 5-(4-biphenylyl)-3-({[4-(methyloxy)phenyl]methyl}oxy)-2-{2-[(methylsulfonyl)oxy]ethyl}pentanoate

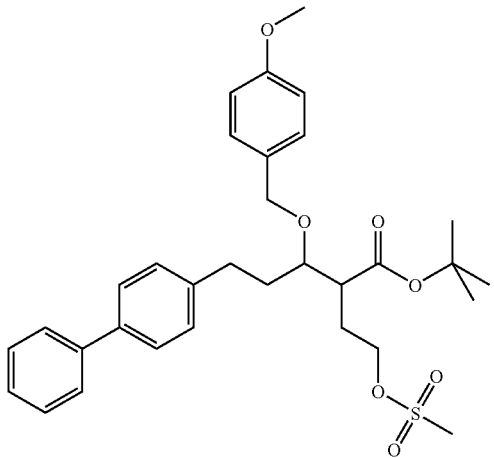

Methanesulfonyl chloride (64 μL, 0.83 mmol) was added in one portion to a stirred solution of 1,1-dimethylethyl 5-(4-biphenylyl)-2-(2-hydroxyethyl)-3-({[4-(methyloxy)phenyl]methyl}oxy) pentanoate (368 mg, 0.751 mmol) and triethylamine (15.4 mg, 209 μL, 1.52 mmol) in dichloromethane (2 mL) at room temperature under nitrogen. After stirring at room temperature for 1 h the crude mixture was partitioned between saturated aqueous citric acid solution (20 mL) and dichloromethane (20 mL). The phases were separated and the organic layer was evaporated to give the title compound (409 mg, 79%) as a yellow oil which was a mixture of diastereomers. LC/MS: 4.08 min; z/e 586, calcd (M+1) 586. $^1$H NMR (400 MHz: CDCl$_3$): 7.50 (6H), 7.25 (4H), 7.15 (1H), 6.90 (2H), 4.50 (2H), 4.25 (2H), 3.80 (3H), 3.75 (1H), 2.95 (3H), 2.90-2.50 (3H), 2.05 (2H), 1.95-1.65 (2H), 1.55-1.35 (9H).

Intermediate 9: 5-(4-Iodo-phenyl)-3-oxo-pentanoic acid tert-butyl ester

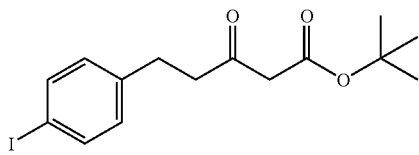

t-butylacetoacetate (1.5 mL, 9.2 mmol) was added dropwise over 2 minutes to a stirred suspension of sodium hydride (60% mineral oil suspension; 400 mg, 10.0 mmol) in tetrahydrofuran at 0° C. under nitrogen. After stirring for 10 minutes n-butyl lithium in hexane (1.6 M; 6.0 mL, 9.6 mmol) was added then stirring continued for a further ten minutes. The resulting solution was treated dropwise with a solution of 4-iodobenzyl bromide (2.97 g, 10.0 mmol) in tetrahydrofuran (4 mL) and then warmed to room temperature. The reaction was stirred for 40 minutes at room temperature and then quenched with 6 M HCl (5 mL). The resulting mixture was extracted with diethyl ether (3×50 mL). The organic phases were combined, washed with brine (50 mL) and dried (MgSO$_4$) then the solvent evaporated under reduced pressure. The residue was purified via flash chromatography on silica gel (1:20 to 1:10 ethyl acetate/cyclohexane) to give the title compound (1.88 g, 54%) as a yellow oil. LC/MS: 3.66 min; z/e 375, calcd (M+1) 375. $^1$H NMR (400 MHz; CDCl$_3$): 7.6 (2H), 6.93 (2H), 3.33 (2H), 2.85 (4H), 1.45 (9H).

Intermediate 10: 1,1-Dimethylethyl 2-(2-{[(1,1-dimethylethyl)(dimethyl)silyl]oxy}ethyl)-5-(4-iodophenyl)-3-oxopentanoate

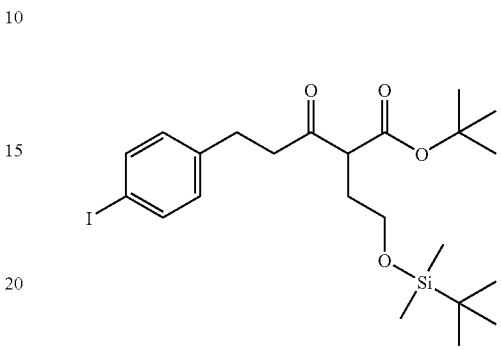

A solution of 5-(4-iodo-phenyl)-3-oxo-pentanoic acid tert-butyl ester (10.0 g, 26.7 mmol) in dimethylformamide (25 mL) was added dropwise over 20 min to a stirred suspension of sodium hydride (60% mineral oil suspension; 1.12 g, 28.0 mmol) in dimethylformamide (25 mL) at 0° C. under nitrogen. After stirring for 20 min (2-bromoethoxy)-t-butyldimethylsilane (7.03 g, 6.31 mL, 29.4 mmol) was added dropwise over 20 min at 0° C. then the reaction heated to 70° C. for 3.5 h. On cooling to room temperature the reaction was quenched by careful addition of water (2 mL) then the volatiles evaporated. The residue was partitioned between saturated aqueous ammonium chloride solution (150 mL) and dichloromethane (150 mL) and the phases separated. The aqueous phase was washed with dichloromethane (3×150 mL) then the organic phases combined, washed with brine (150 mL), dried (sodium sulfate) and the solvent evaporated. The residue was chromatographed on silica gel (25% diethyl ether:cyclohexane) to give the title compound (10.0 g, 70%) as colourless oil which was a mixture of diastereomers. LC/MS: 4.55 min; z/e 533, calcd (M+1) 533. $^1$H NMR (400 MHz; CDCl$_3$): 7.55 (2H), 6.90 (2H), 3.55 (3H), 2.85 (4H), 2.15 (2H minor), 1.95 (2H major), 1.40 (9H), 0.85 (9H), 0.5 (6H).

Intermediate 11: 1,1-Dimethylethyl 2-(2-{[(1,1-dimethylethyl)(dimethyl)silyl]oxy}ethyl)-3-hydroxy-5-(4-iodophenyl)pentanoate

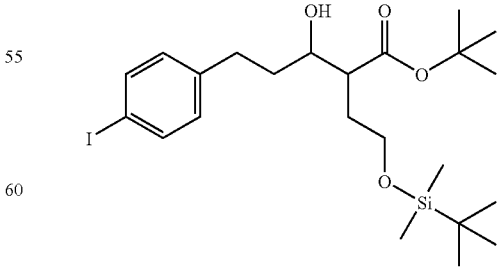

Sodium borohydride (0.59 g, 15.6 mmol) was added portion wise to a stirred solution of 1,1-dimethylethyl 2-(2-{[(1,1-dimethylethyl)(dimethyl)silyl]oxy}ethyl)-5-(4-iodophenyl)-3-oxopentanoate (7.55 g, 14.2 mmol) in methanol (100 mL) at 0° C. under nitrogen. On completion of addition stirring was continued for 1.5 h then the reaction was quenched with saturated aqueous ammonium chloride solution (100 mL). The resulting mixture was extracted with diethyl ether (3×200 mL) then the organic layers were combined, washed with brine (100 mL), dried (sodium sulfate) and the solvent evaporated. The residue was chromatographed on silica gel (25% to 50% diethyl ether:cyclohexane) to give the title compound (5.14 g, 68%) as a colourless oil which was a mixture of diastereomers.

LC/MS: 4.72 min; z/e 535, calcd (M+1) 535. $^1$H NMR (400 MHz: CDCl$_3$): 7.55 (2H), 6.95 (2H), 3.85-3.55 (3H), 3.30 (1H minor), 3.00 (1H major), 2.80 (1H), 2.65 (1H), 2.55 (1H major), 2.50 (1H minor), 1.95-1.65 (4H), 1.45 (9H), 0.90 (9H), 0.5 (6H).

Intermediate 12: 1,1-Dimethylethyl 2-(2-{[(1,1-dimethylethyl)(dimethyl)silyl]oxy}ethyl)-5-(4-iodophenyl)-3-({[4-(methyloxy)phenyl]methyl}oxy)pentanoate

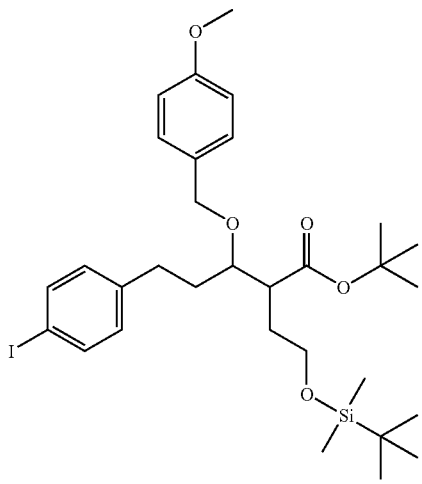

Boron trifluoride etherate (5.0 µL, 39 µmol) was added to a stirred solution of 1,1-dimethylethyl 2-(2-{[(1,1-di methylethyl)(dimethyl)silyl]oxy}ethyl)-3-hydroxy-5-(4-iodophenyl)pentanoate (5.14 g, 9.63 mmol) and 4-methoxybenzyl 2,2,2-trichloroethanimidoate (4.05 g, 14.4 mmol) in tetrahydrofuran (40 mL) at 0° C. under nitrogen. The reaction was allowed to warm to room temperature at which stirring was continued for 2 h. A further portion of boron trifluoride etherate (5.0 µL, 39 µmol) was then added and stirring was continued at room temperature for a further 2 h. Two further additions of boron trifluoride etherate (5.0 µL, 39 µmol) followed by stirring at room temperature for 2 h were carried out before evaporation of the solvent. The residue was chromatographed on silica gel (0% to 10% diethyl ether:cyclohexane) to give the title compound (4.14 g, 66%) as a yellow oil which was a mixture of diastereomers. LC/MS: 4.78 min; z/e 655, calcd (M+1) 655. $^1$H NMR (400 MHz: CDCl$_3$): 7.55 (2H), 7.25 (2H), 6.90 (2H), 6.80 (2H), 4.55 (1H), 4.35 (1H), 3.80 (3H), 3.65 (1H), 3.55 (1H), 2.95 (1H major), 2.80 (1H minor), 2.70 (1H), 2.55 (1H), 1.95-1.60 (4H), 1.45 (9H), 0.85 (9H), 0.5 (6H).

Intermediate 13: 1,1-Dimethylethyl 2-(2-hydroxyethyl)-5-(4-iodophenyl)-3-({[4-(methyloxy)phenyl]methyl}oxy)pentanoate

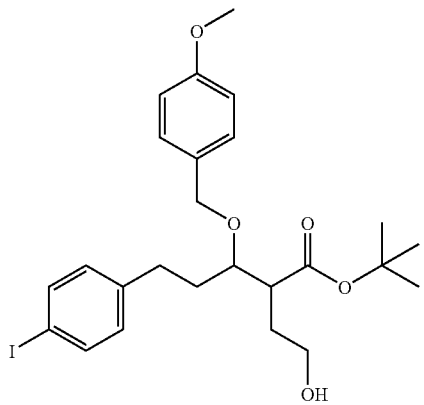

A solution of tetra-n-butylammonium fluoride (1.0 M in THF; 7.0 mL, 7.0 mmol) was added dropwise over 15 min to a stirred solution of 1,1-dimethylethyl 2-(2-{[(1,1-dimethylethyl)(dimethyl)silyl]oxy}ethyl)-5-(4-iodophenyl)-3-({[4-(methyloxy)phenyl]methyl}oxy) pentanoate (4.14 g, 6.33 mmol) in tetrahydrofuran (25 mL) at 0° C. under nitrogen. The reaction was allowed to warm to room temperature at which stirring was continued for 2 h. The volatiles were evaporated and the residue partitioned between ethyl acetate (100 mL) and water (100 mL). The phases were separated and the aqueous layer was washed with ethyl acetate (3×100 mL). The organic layers were combined, washed with brine (100 mL), dried (magnesium sulfate) and the solvent evaporated. The residue was chromatographed on silica gel (25% to 50% ethyl acteate: cyclohexane) to give the title compound (2.87 g, 84%) as a yellow oil which was a mixture of diastereomers. LC/MS: 3.86 min; z/e 541, calcd (M+1) 541. $^1$H NMR (400 MHz: CDCl$_3$): 7.55-7.25 (4H), 6.90-6.75 (4H), 4.55-4.35 (2H), 3.80 (3H), 3.65 (3H), 2.90-2.45 (3H), 1.90-1.60 (4H), 1.35 (9H).

Intermediate 14 1,1-Dimethylethyl 5-(4-iodophenyl)-3-({[4-(methyloxy)phenyl]methyl}oxy)-2-{2-[(methylsulfonyl)oxy]ethyl}pentanoate

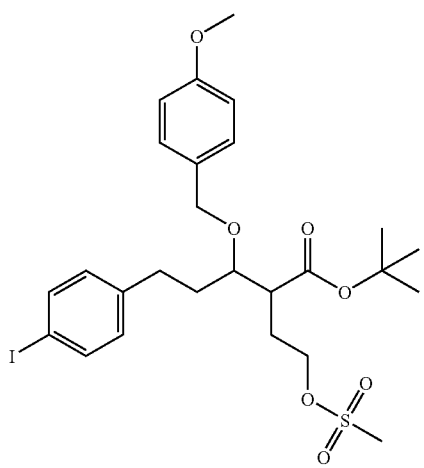

Methanesulfonyl chloride (315 μL, 5.91 mmol) was added in one portion to a stirred solution of 1,1-dimethylethyl 2-(2-hydroxyethyl)-5-(4-iodophenyl)-3-({[4-(methyloxy)phenyl]methyl}oxy) pentanoate (2.00 g, 3.70 mmol) and triethylamine (1.03 mL, 7.39 mmol) in dichloromethane (10 mL) at room temperature under nitrogen. After stirring at room temperature for 1 h the crude mixture was partitioned between saturated aqueous citric acid solution (40 mL) and dichloromethane (40 mL). The phases were separated and the organic layer was evaporated to give the title compound (2.3 g, 100%) as a yellow oil which was a mixture of diastereomers. LC/MS: 4.00 min; z/e 636, calcd (M+18) 636. $^1$H NMR (400 MHz: CDCl$_3$): 7.60-7.20 (4H), 6.90-6.75 (4H), 4.60-4.20 (5H), 3.80 (3H), 2.95 (3H), 2.90-2.45 (3H), 2.10-1.70 (4H), 1.40 (9H).

Intermediate 15: 1,1-Dimethylethyl 2-[2-(1,3-dioxo-1,3-dihydro-2H-isoindol-2-yl)ethyl]-5-(4-iodophenyl)-3-({[4-(methyloxy)phenyl]methyl}oxy)pentanoate

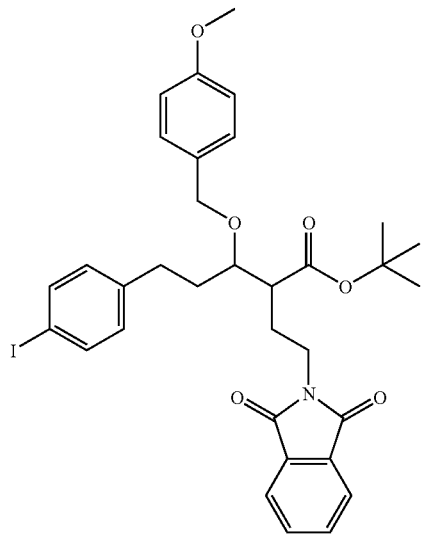

Potassium phthalimide (0.33 g, 2.2 mmol) was added in one portion to a stirred solution of 1,1-dimethylethyl 5-(4-iodophenyl)-3-({[4-(methyloxy)phenyl]methyl}oxy)-2-{2-[(methylsulfonyl)oxy]ethyl}pentanoate (1.15 g, 1.86 mmol) in dimethylformamide (6 mL) at room temperature under nitrogen. The resulting solution was heated at 80° C. for 1 h 45 min then cooled to room temperature. The volatiles were evaporated and the residue partitioned between dichloromethane (50 mL) and water (50 mL). The layers were separated and the organic phase evaporated to dryness. The residue was chromatographed on silica gel (50% ethyl acetate:cyclohexane) to give the title compound (0.26 g, 21%) as a yellow oil which was a mixture of diastereoisomers. LC/MS: 4.29 min; z/e 687, calcd (M+18) 687. $^1$H NMR (400 MHz: CDCl$_3$): 7.85 (2H), 7.70 (2H), 7.55-7.20 (4H), 6.90-6.75 (4H), 4.55-4.30 (2H), 3.80 (3H), 3.75 (1H), 3.65 (2H), 2.80-2.45 (3H), 2.10-1.50 (4H), 1.40 (9H).

Intermediate 16 1,1-Dimethylethyl 5-(4-iodophenyl)-2-[2-(3-methyl-2,4-dioxo-3,4-dihydro-1(2H)-pyrimidinyl)ethyl]-3-({[4-(methyloxy)phenyl]methyl}oxy) pentanoate

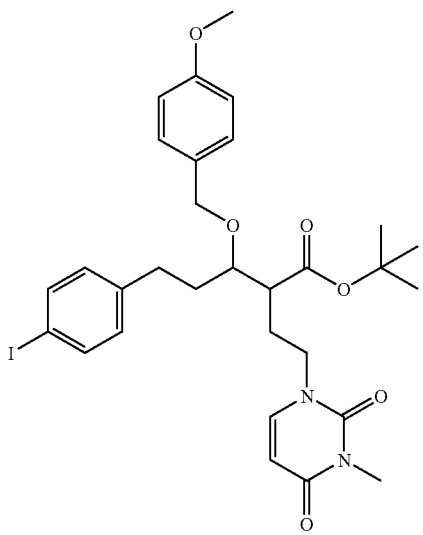

3-Methyl-2,4(1H,3H)-pyrimidinedione (0.28 g, 2.2 mmol) was added in one portion to a stirred suspension of sodium hydride (60% suspension in mineral oil; 80 mg, 2.0 mmol) in dimethylformamide (3 mL) at room temperature under nitrogen. The resulting suspension was stirred for 5 min then a solution of 1,1-dimethylethyl 5-(4-iodophenyl)-3-({[4-(methyloxy)phenyl]methyl}oxy)-2-{2-[(methylsulfonyl)oxy]ethyl}pentanoate (1.15 g, 1.86 mmol) in dimethylformamide (3 mL) was added in one portion. The resulting solution was heated at 80° C. for 1 h 45 min then cooled to room temperature. The volatiles were evaporated and the residue partitioned between dichloromethane (50 mL) and water (50 mL). The layers were separated and the organic phase evaporated to dryness. The residue was chromatographed on silica gel (10% methanol:dichloromethane) to give the title compound (0.33 g, 27%) as a yellow oil which was a mixture of diastereomers. LC/MS: 3.87 min; z/e 649, calcd (M+1) 649. $^1$H NMR (400 MHz: CDCl$_3$): 7.55 (2H), 7.25 (2H), 7.10 (1H), 6.90-6.75 (4H), 5.70 (1H), 4.40 (2H), 3.85-3.60 (6H), 3.75-2.45 (3H), 2.00-1.70 (4H), 1.40 (9H).

Intermediate 17 2-[2-(1,3-Dioxo-1,3-dihydro-2H-isoindol-2-yl)ethyl]-3-hydroxy-5-(4-iodophenyl) pentanoic acid

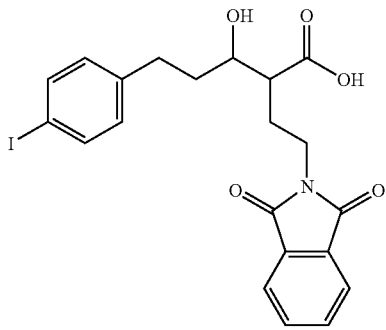

Trifluoroacetic acid (5 mL) was added in one portion to a stirred solution of 1,1-dimethylethyl 2-[2-(1,3-dioxo-1,3-dihydro-2H-isoindol-2-yl)ethyl]-5-(4-iodophenyl)-3-({[4-(methyloxy)phenyl]methyl}oxy)pentanoate (261 mg, 0.390 mmol) in dichloromethane (5 mL) at room temperature under nitrogen. The resulting solution was stirred for 45 min then the volatiles evaporated to give the title compound (192 mg, 100%) as a yellow solid which was a mixture of diastereomers. LC/MS: 3.32 min; z/e 493, calcd (M+1) 493. $^1$H NMR (400 MHz: CDCl$_3$): 7.85 (4H), 7.55 (2H), 6.95 (2H), 4.90 (1H), 3.80-3.50 (3H), 2.70-2.20 (3H), 1.85 (2H), 1.55 (2H).

Intermediate 18: 3-Hydroxy-5-(4-iodophenyl)-2-[2-(3-methyl-2,4-dioxo-3,4-dihydro-1(2H)-pyrimidinyl)ethyl]pentanoic acid

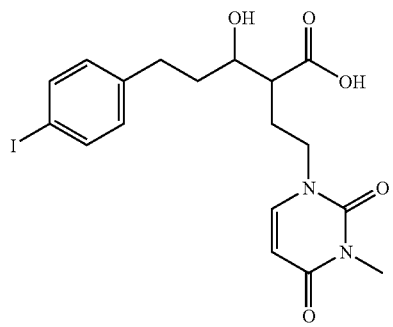

Prepared by an analogous reaction to intermediate 17. LC/MS: 2.85 min; z/e 473, calcd (M+1) 473.

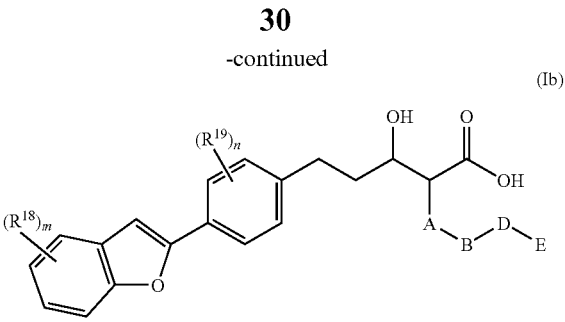

(Ib)

wherein:

T is absent or represents —O—, —S—, —NR$^{16}$ or —CR$^{16}$R$^{17}$;

--- represents optional bonds;

G$^1$ and G$^2$ each independently represents —CH— or —N—;

A represents bond, —C$_{1-6}$alkyl or —CH=CH—C$_{1-4}$alkyl;

B represents bond, —O—, —S—, —SO—, —SO$_2$—, —CO—, —CR$^7$R$^8$, —CO$_2$R$^{14}$, —CONR$^{14}$R$^{15}$, —N(COR$^{14}$)(COR$^{15}$), —N(SO$_2$R$^{14}$)(COR$^{15}$), or —NR$^{14}$R$^{15}$;

wherein R$^7$ and R$^8$ each independently represent H, halo, C$_{1-6}$ alkyl or C$_{1-4}$ alkylaryl;

wherein R$^{14}$ and R$^{15}$ each independently represent H, C$_{1-6}$ alkyl, C$_{1-4}$ alkylaryl or C$_{1-4}$ alkylheteroaryl or together with the functionality to which they are attached R$^{14}$ and R$^{15}$ form a heterocyclic or fused

---

---

The invention claimed is:

1. A method for treating chronic obstructive pulmonary disease (COPD), which comprises administering an effective amount of a compound of formula (Ia) or (Ib) to a human subject in need thereof:

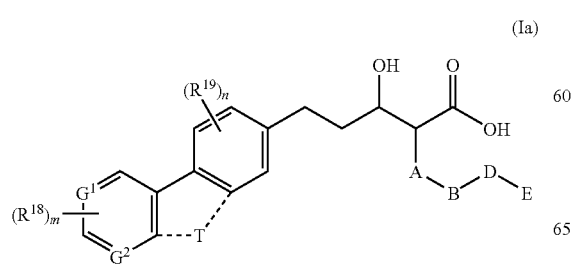

(Ia)

heterocyclic group which may contain one or more further atoms selected from C, O, N and S;

D represents bond, or —C$_{1-6}$ alkyl;

E represents substituted aryl or substituted or unsubstituted heteroaryl;

wherein:

heteroaryl is selected from mono- or bicyclic heterocyclic aromatic containing 1-3 hetero atoms selected from nitrogen, oxygen and sulphur;

wherein aryl or heteroaryl is substituted by one or more substituents selected from C$_{1-6}$ alkyl, C$_{2-6}$ alkenyl, halogen, C$_{1-6}$ alkoxy, cyano, hydroxy, nitro, amino, —N(CH$_3$)$_2$, —NHCOC$_{1-6}$ alkyl, —OCF$_3$, —CF$_3$, —COOC$_{1-6}$ alkyl, —OCHCF$_2$, —SCF$_3$, —CONR$^5$R$^6$, —SO$_2$N(CH$_3$)$_2$, —SO$_2$CH$_3$ or —SCH$_3$ groups, or unsubstituted or substituted fused cycloalkyl or heterocyclic rings, wherein fused cycloalkyl or heterocyclic rings optionally are substituted by carbonyl groups;

wherein R⁵ and R⁶ each independently represent H, $C_{1-6}$ alkyl or $C_{1-4}$ alkylaryl;

R¹⁸ and R¹⁹ each independently represents halo, cyano, nitro, —OR¹⁶, —SR¹⁶, —COR¹⁶, —NR¹⁷COR¹⁶, —CONR¹⁶R¹⁷, optionally substituted phenoxy or —$C_{1-6}$alkyl optionally substituted by —OR¹⁶;

wherein:
R¹⁶ represents H, —$C_{1-6}$ alkyl or —$C_{1-4}$ alkylaryl;
wherein R¹⁷ represents H or —$C_{1-6}$ alkyl;
m and n each independently represents 0 or an integer 1, 2 or 3; or
a pharmaceutically acceptable salt thereof.

2. The method for treatment of chronic obstructive pulmonary disease (COPD) according to claim 1, wherein the compound of formula (Ia) or (Ib) is selected from:

5-Biphenyl-4-yl-2-[2-(1,3-dioxo-1,3-dihydro-2H-isoindol-2-yl)ethyl]-3-hydroxypentanoic acid;
5-Biphenyl-4-yl-3-hydroxy-2-[2-(3-methyl-2,6-dioxo-3,6-dihydropyrimidin-1(2H)-yl)ethyl]pentanoic acid;
5-Biphenyl-4-yl-3-hydroxy-2-[2-(3-methyl-2,4-dioxo-3,4-dihydropyrimidin-1(2H)-yl)ethyl]pentanoic acid;
5-(4'-Acetylbiphenyl-4-yl)-3-hydroxy-2-[2-(3-methyl-2,4-dioxo-3,4-dihydropyrimidin-1(2H)-yl)ethyl]pentanoic acid;
3-Hydroxy-2-[2-(3-methyl-2,4-dioxo-3,4-dihydropyrimidin-1(2H)-yl)ethyl]-5-(4-pyrimidin-5-ylphenyl)pentanoic acid;
3-Hydroxy-2-[2-(3-methyl-2,4-dioxo-3,4-dihydropyrimidin-1(2H)-yl)ethyl]-5-[4'-(trifluoromethoxy)biphenyl-4-yl]pentanoic acid;
5-[4-(1-Benzofuran-2-yl)phenyl]-2-[2-(1,3-dioxo-1,3-dihydro-2H-isoindol-2-yl)ethyl]-3-hydroxypentanoic acid;
2-[2-(1,3Dioxo-1,3-dihydro-2H-isoindol-2-yl)ethyl]-3-hydroxy-5-[4'-(trifluoromethoxy)biphenyl-4-yl]pentanoic acid;
2-[2-(1,3-Dioxo-1,3-dihydro-2H-isoindol-2-yl)ethyl]-3-hydroxy-5-[4'-(methylthio)biphenyl-4-yl]pentanoic acid;
5-(4'-Cyanobiphenyl-4-yl)-2-[2-(1,3-dioxo-1,3-dihydro-2H-isoindol-2-yl)ethyl]-3-hydroxypentanoic acid;
5-(4'-Acetylbiphenyl-4-yl)-2-[2-(1,3-dioxo-1,3-dihydro-2H-isoindol-2-yl)ethyl]-3-hydroxypentanoic acid;
2-[2-(1,3-Dioxo-1,3-dihydro-2H-isoindol-2-yl)ethyl]-3-hydroxy-5-(4-pyrimidin-5-ylphenyl)pentanoic acid; or
a pharmaceutically acceptable salts thereof.

3. A method for treating chronic obstructive pulmonary disease (COPD), which comprises administering an effective amount of a compound of formula (Ic) to a human subject in need thereof:

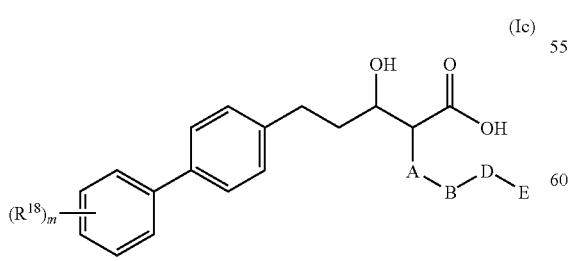

(Ic)

wherein:
A represents bond, —$C_{1-6}$alkyl or —CH═CH—$C_{1-4}$alkyl;

B represents bond, —O—, —S—, —SO—, —SO₂—, —CO—, —CR⁷R⁸, —CO₂R¹⁴, —CONR¹⁴R¹⁵, —N(COR¹⁴)(COR¹⁵), —N(SO₂R¹⁴)(COR¹⁵), or —NR¹⁴R¹⁵;

wherein:
R⁷ and R⁸ each independently represent H, halo, $C_{1-6}$ alkyl or $C_{1-4}$ alkylaryl;
R¹⁴ and R¹⁵ each independently represent H, $C_{1-6}$ alkyl, $C_{1-4}$ alkylaryl or $C_{1-4}$ alkylheteroaryl or together with the functionality to which they are attached R¹⁴ and R¹⁵ form a heterocyclic or fused heterocyclic group which contain one or more further atoms selected from C, O, N or S;

D represents bond, or —$C_{1-6}$ alkyl;
E represents substituted aryl or substituted or unsubstituted heteroaryl;
wherein heteroaryl is selected from mono- or bicyclic heterocyclic aromatic containing 1-3 hetero atoms selected from nitrogen, oxygen and sulphur;
wherein aryl or heteroaryl is substituted by one or more substituents selected from $C_{1-6}$ alkyl, $C_{2-6}$ alkenyl, halogen, $C_{1-6}$ alkoxy, cyano, hydroxy, nitro, amino, —N(CH₃)₂, —NHCOC₁₋₆ alkyl, —OCF₃, —CF₃, —COOC₁₋₆ alkyl, —OCHCF₂, —SCF, —CONR⁵R⁶, —SO₂N(CH₃)₂, —SO₂CH₃ or —SCH₃ groups, or unsubstituted or substituted fused cycloalkyl or heterocyclic rings;
wherein fused cycloalkyl or heterocyclic rings optionally are substituted by carbonyl groups;
wherein R⁵ and R⁶ each independently represent H, $C_{1-6}$ alkyl or $C_{1-4}$ alkylaryl;

R¹⁸ represents halo, cyano, nitro, —OR¹⁶, —SR¹⁶, —COR¹⁶, —NR¹⁷COR¹⁶, —CONR¹⁶R¹⁷, optionally substituted phenoxy or —$C_{1-6}$alkyl optionally substituted by —OR¹⁶;

wherein:
R¹⁶ represents H, —$C_{1-6}$ alkyl or —$C_{1-4}$ alkylaryl;
R¹⁷ represents H or —$C_{1-6}$ alkyl;
m and n each independently represents 0 or an integer 1, 2 or 3; or
a pharmaceutically acceptable salt thereof.

4. A method for treating chronic obstructive pulmonary disease (COPD), which comprises administering an effective amount of a compound of formula (Id) to a human subject in need thereof:

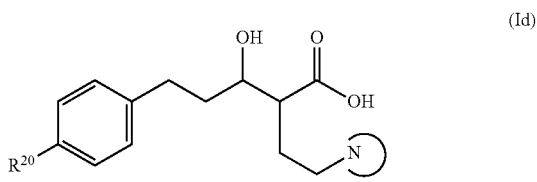

(Id)

wherein:
R²⁰ represents a substituted or unsubstituted aryl or heteroaryl group selected from phenyl, benzofuraryl and pyrimidinyl; and

represents a substituted aryl or a substituted or unsubstituted heteroaryl group comprising at least one nitrogen atom;
  wherein heteroaryl is selected from mono- or bicyclic heterocyclic aromatic containing 1-3 hetero atoms selected from nitrogen, oxygen and sulphur;
    wherein aryl or heteroaryl is substituted by one or more substituents selected from $C_{1-6}$ alkyl, $C_{2-6}$ alkenyl, halogen, $C_{1-6}$ alkoxy, cyano, hydroxy, nitro, amino, —$N(CH_3)_2$, —$NHCOC_{1-6}$ alkyl, —$OCF_3$, —$CF_3$, —$COOC_{1-6}$ alkyl, —$OCHCF_2$, —$SCF_3$, —$CONR^5R^6$, —$SO_2N(CH_3)_2$, —$SO_2CH_3$ or —$SCH_3$ groups, or unsubstituted or substituted fused cycloalkyl or heterocyclic rings;
    wherein fused cycloalkyl or heterocyclic rings optionally are substituted by carbonyl groups;
  wherein $R^5$ and $R^6$ each independently represent H, $C_{1-6}$ alkyl or $C_{1-4}$ alkylaryl; or
a pharmaceutically acceptable salt thereof.

5. A method for treating idiopathic pulmonary fibrosis, which comprises administering to a human subject in need thereof an effective amount of a compound of formula (Ia) or (Ib):

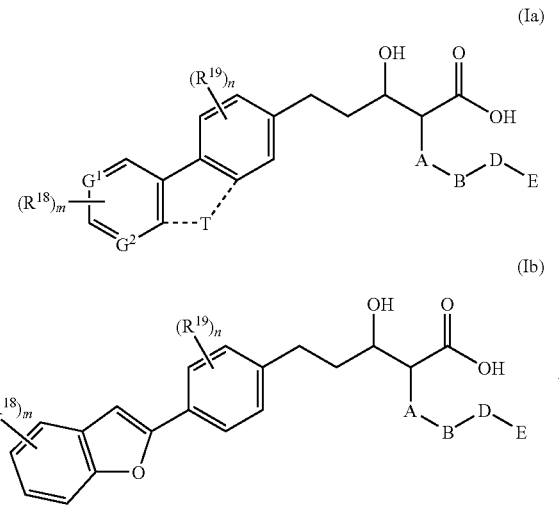

wherein:
T is absent or represents —O—, —S—, —$NR^{16}$ or —$CR^{16}R^{17}$;
--- represents optional bonds;
$G^1$ and $G^2$ each independently represents —CH— or —N—;
A represents bond, —$C_{1-6}$alkyl or —CH=CH—$C_{1-4}$alkyl;
B represents bond, —O—, —S—, —SO—, —$SO_2$—, —CO—, —$CR^7R^8$, —$CO_2R^{14}$, —$CONR^{14}R^{15}$, —$N(COR^{14})(COR^{15})$, —$N(SO_2R^{14})(COR^{15})$, or —$NR^{14}R^{15}$;
wherein:
  $R^7$ and $R^8$ each independently represent H, halo, $C_{1-6}$ alkyl or $C_{1-4}$ alkylaryl;
  $R^{14}$ and $R^{15}$ each independently represent H, $C_{1-6}$ alkyl, $C_{1-4}$ alkylaryl or $C_{1-4}$ alkylheteroaryl or together with the functionality to which they are attached $R^{14}$ and $R^{15}$ form a heterocyclic or fused heterocyclic group which contain one or more further atoms selected from C, O, N or S;

D represents bond, or —$C_{1-6}$ alkyl;
E represents substituted aryl or substituted or unsubstituted heteroaryl;
  wherein heteroaryl is selected from mono- or bicyclic heterocyclic aromatic containing 1-3 hetero atoms selected from nitrogen, oxygen and sulphur;
    wherein aryl or heteroaryl is substituted by one or more substituents selected from $C_{1-6}$ alkyl, $C_{2-6}$ alkenyl, halogen, $C_{1-6}$ alkoxy, cyano, hydroxy, nitro, amino, —$N(CH_3)_2$, —$NHCOC_{1-6}$ alkyl, —$OCF_3$, —$CF_3$, —$COOC_{1-6}$ alkyl, —$OCHCF_2$, —$SCF_3$, —$CONR^5R^6$, —$SO_2N(CH_3)_2$, —$SO_2CH_3$ or —$SCH_3$ groups, or unsubstituted or substituted fused cycloalkyl or heterocyclic rings;
    wherein fused cycloalkyl or heterocyclic rings optionally are substituted by carbonyl groups;
  wherein $R^5$ and $R^6$ each independently represent H, $C_{1-6}$ alkyl or $C_{1-4}$ alkylaryl;
$R^{18}$ and $R^{19}$ each independently represents halo, cyano, nitro, —$OR^{16}$, —$SR^{16}$, —$COR^{16}$, —$NR^{17}COR^{16}$, —$CONR^{16}R^{17}$, optionally substituted phenoxy or —$C_{1-6}$alkyl optionally substituted by —$OR^{16}$;
wherein:
  $R^{16}$ represents H, —$C_{1-6}$ alkyl or —$C_{1-4}$ alkylaryl;
  $R^{17}$ represents H or —$C_{1-6}$ alkyl;
m and n each independently represents 0 or an integer 1, 2 or 3; or
a pharmaceutically acceptable salt thereof.

6. The method for treating idiopathic pulmonary fibrosis according to claim 5, wherein the compound of formula (Ia) or (Ib) is selected from:
  5-Biphenyl-4-yl-2-[2-(1,3-dioxo-1,3-dihydro-2H-isoindol-2-yl)ethyl]-3-hydroxypentanoic acid;
  5-Biphenyl-4-yl-3-hydroxy-2-[2-(3-methyl-2,6-dioxo-3,6-dihydropyrimidin-1(2H)-yl)ethyl]pentanoic acid;
  5-Biphenyl-4-yl-3-hydroxy-2-[2-(3-methyl-2,4-dioxo-3,4-dihydropyrimidin-1(2H)-yl)ethyl]pentanoic acid;
  5-(4'-Acetylbiphenyl-4-yl)-3-hydroxy-2-[2-(3-methyl-2,4-dioxo-3,4-dihydropyrimidin-1(2H)-yl)ethyl]pentanoic acid;
  3-Hydroxy-2-[2-(3-methyl-2,4-dioxo-3,4-dihydropyrimidin-1(2H)-yl)ethyl]-5-(4-pyrimidin-5-ylphenyl)pentanoic acid;
  3-Hydroxy-2-[2-(3-methyl-2,4-dioxo-3,4-dihydropyrimidin-1(2H)-yl)ethyl]-5-[4'-(trifluoromethoxy)biphenyl-4-yl]pentanoic acid;
  5-[4-(1-Benzofuran-2-yl)phenyl]-2-[2-(1,3-dioxo-1,3-dihydro-2H-isoindol-2-yl)ethyl]-3-hydroxypentanoic acid;
  2-[2-(1,3-Dioxo-1,3-dihydro-2H-isoindol-2-yl)ethyl]-3-hydroxy-5-[4'-(trifluoromethoxy)biphenyl-4-yl]pentanoic acid;
  2-[2-(1,3-Dioxo-1,3-dihydro-2H-isoindol-2-yl)ethyl]-3-hydroxy-5-[4'-(methylthio)biphenyl-4-yl]pentanoic acid;
  5-(4'-Cyanobiphenyl-4-yl)-2-[2-(1,3-dioxo-1,3-dihydro-2H-isoindol-2-yl)ethyl]-3-hydroxypentanoic acid;
  5-(4'-Acetylbiphenyl-4-yl)-2-[2-(1,3-dioxo-1,3-dihydro-2H-isoindol-2-yl)ethyl]-3-hydroxypentanoic acid;
  2-[2-(1,3-Dioxo-1,3-dihydro-2H-isoindol-2-yl)ethyl]-3-hydroxy-5-(4-pyrimidin-5-ylphenyl)pentanoic acid; or
a pharmaceutically acceptable salt thereof.

7. A method for treating idiopathic pulmonary fibrosis, which comprises administering to a human subject in need thereof an effective amount of a compound of formula (Ic):

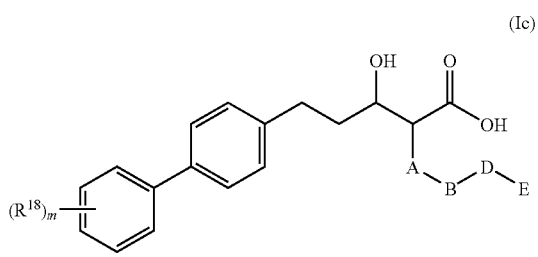

(Ic)

wherein:
A represents bond, —C$_{1-6}$alkyl or —CH=CH—C$_{1-4}$alkyl;
B represents bond, —O—, —S—, —SO—, —SO$_2$—, —CO—, —CR$^7$R$^8$, —CO$_2$R$^{14}$, —CONR$^{14}$R$^{15}$, —N(COR$^{14}$)(COR$^{15}$), —N(SO$_2$R$^{14}$)(COR$^{15}$), or —NR$^{14}$R$^{15}$;
  wherein R$^7$ and R$^8$ each independently represent H, halo, C$_{1-6}$ alkyl or C$_{1-4}$ alkylaryl;
  wherein R$^{14}$ and R$^{15}$ each independently represent H, C$_{1-6}$ alkyl, C$_{1-4}$ alkylaryl or C$_{1-4}$ alkylheteroaryl or together with the functionality to which they are attached R$^{14}$ and R$^{15}$ form a heterocyclic or fused heterocyclic group which contain one or more further atoms selected from C, O, N and S;
D represents bond, or —C$_{1-6}$ alkyl;
E represents substituted aryl or substituted or unsubstituted heteroaryl;
  wherein heteroaryl is selected from mono- or bicyclic heterocyclic aromatic containing 1-3 hetero atoms selected from nitrogen, oxygen and sulphur;
    wherein aryl or heteroaryl is substituted by one or more substituents selected from C$_{1-6}$ alkyl, C$_{2-6}$ alkenyl, halogen, C$_{1-6}$ alkoxy, cyano, hydroxy, nitro, amino, —N(CH$_3$)$_2$, —NHCOC$_{1-6}$ alkyl, —OCF$_3$, —CF$_3$, —COOC$_{1-6}$ alkyl, —OCHCF$_2$, —SCF$_3$, —CONR$^5$R$^6$, —SO$_2$N(CH$_3$)$_2$, —SO$_2$CH$_3$ or —SCH$_3$ groups, or unsubstituted or substituted fused cycloalkyl or heterocyclic rings, wherein fused cycloalkyl or heterocyclic rings optionally are substituted by carbonyl groups;
    wherein R$^5$ and R$^6$ each independently represent H, C$_{1-6}$ alkyl or C$_{1-4}$ alkylaryl;
R$^{18}$ represents halo, cyano, nitro, —OR$^{16}$, —SR$^{16}$, —COR$^{16}$, —NR$^{17}$COR$^{16}$, —CONR$^{16}$R$^{17}$, optionally substituted phenoxy or —C$_{1-6}$alkyl optionally substituted by —OR$^{16}$;

wherein:
R$^{16}$ represents H, —C$_{1-6}$ alkyl or —C$_{1-4}$ alkylaryl;
R$^{17}$ represents H or —C$_{1-6}$ alkyl;
m and n each independently represents 0 or an integer 1, 2 or 3; or
a pharmaceutically acceptable salt thereof.

8. A method for treating idiopathic pulmonary fibrosis, which comprises administering to a human subject in need thereof an effective amount of a compound of formula (Id):

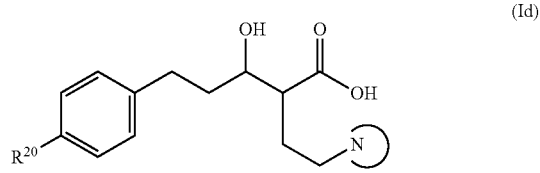

(Id)

wherein:
R$^{20}$ represents a substituted or unsubstituted aryl or heteroaryl group selected from phenyl, benzofuraryl and pyrimidinyl; and

represents a substituted aryl or a substituted or unsubstituted heteroaryl group comprising at least one nitrogen atom;
  wherein heteroaryl is selected from mono- or bicyclic heterocyclic aromatic containing 1-3 hetero atoms selected from nitrogen, oxygen and sulphur;
    wherein aryl or heteroaryl is substituted by one or more substituents selected from C$_{1-6}$ alkyl, C$_{2-6}$ alkenyl, halogen, C$_{1-6}$ alkoxy, cyano, hydroxy, nitro, amino, —N(CH$_3$)$_2$, —NHCOC$_{1-6}$ alkyl, —OCF$_3$, —CF$_3$, —COOC$_{1-6}$ alkyl, —OCHCF$_2$, —SCF$_3$, —CONR$^5$R$^6$, —SO$_2$N(CH$_3$)$_2$, —SO$_2$CH$_3$ or —SCH$_3$ groups, or unsubstituted or substituted fused cycloalkyl or heterocyclic rings, wherein fused cycloalkyl or heterocyclic rings optionally are substituted by carbonyl groups;
  wherein R$^5$ and R$^6$ each independently represent H, C$_{1-6}$ alkyl or C$_{1-4}$ alkylaryl; or
a pharmaceutically acceptable salt thereof.

\* \* \* \* \*